US012337024B2

(12) United States Patent
Radhakrishnan et al.

(10) Patent No.: US 12,337,024 B2
(45) Date of Patent: Jun. 24, 2025

(54) LARAZOTIDE FORMULATIONS

(71) Applicant: Interlude Biopharma Co., Miami, FL (US)

(72) Inventors: Balasingham Radhakrishnan, Raleigh, NC (US); Jay P. Madan, Raleigh, NC (US); Gary F. Musso, Raleigh, NC (US)

(73) Assignee: Interlude Biopharma Co., Miami, FL (US)

( * ) Notice: Subject to any disclaimer, the term of this patent is extended or adjusted under 35 U.S.C. 154(b) by 133 days.

(21) Appl. No.: 17/635,441

(22) PCT Filed: Aug. 14, 2020

(86) PCT No.: PCT/US2020/046272
§ 371 (c)(1),
(2) Date: Feb. 15, 2022

(87) PCT Pub. No.: WO2021/034629
PCT Pub. Date: Feb. 25, 2021

(65) Prior Publication Data
US 2022/0331392 A1 Oct. 20, 2022

Related U.S. Application Data

(60) Provisional application No. 63/009,768, filed on Apr. 14, 2020, provisional application No. 62/888,052, filed on Aug. 16, 2019.

(51) Int. Cl.
A61K 38/08 (2019.01)
A61K 9/16 (2006.01)
(Continued)

(52) U.S. Cl.
CPC ............ A61K 38/08 (2013.01); A61K 9/1635 (2013.01); A61K 9/1652 (2013.01); A61K 9/282 (2013.01);
(Continued)

(58) Field of Classification Search
None
See application file for complete search history.

(56) References Cited

U.S. PATENT DOCUMENTS 8,034,776 B2 * 10/2011 Fasano ................. A61K 9/0053
514/21.7
8,933,197 B2 * 1/2015 Stemmer ................... A61P 5/24
530/324

(Continued)

FOREIGN PATENT DOCUMENTS

WO 2021034629 A1 2/2021

OTHER PUBLICATIONS

Jose et al., Colon Targeted Drug Delivery: Different Approaches. J. Young Pharm. vol. 1:1, p. 13-19 (Year: 2009).*

(Continued)

Primary Examiner — Lakshmi S Channavajjala
(74) Attorney, Agent, or Firm — Morgan, Lewis & Bockius LLP

(57) ABSTRACT

The present invention provides, in part, compositions comprising a peptide that is larazotide or larazotide derivative, or salt thereof, contained within a matrix that provides for controlled release and sustained release formulations. The present invention contemplates that these compositions, formulations and methods can be useful for treating diseases and disorders of the small bowel.

17 Claims, 15 Drawing Sheets

Specification includes a Sequence Listing.

(51) Int. Cl.
   *A61K 9/28* (2006.01)
   *A61P 1/04* (2006.01)
(52) U.S. Cl.
   CPC .......... *A61K 9/2846* (2013.01); *A61K 9/2893* (2013.01); *A61P 1/04* (2018.01)

(56) References Cited

U.S. PATENT DOCUMENTS

| | | |
|---|---|---|
| 11,058,902 B2 * | 7/2021 | Madan .................... A61K 45/06 |
| 11,278,587 B2 * | 3/2022 | Madan ................ C07K 16/2818 |
| 2003/0017203 A1 | 1/2003 | Crotts et al. |
| 2010/0104825 A1 | 4/2010 | Campbell et al. |
| 2015/0137399 A1 | 5/2015 | Coulter |
| 2016/0022760 A1 | 1/2016 | Perrow et al. |
| 2017/0121454 A1 | 5/2017 | Saltzman |

OTHER PUBLICATIONS

International Search Report for International Patent Application No. PCT/US20/46272 dated Nov. 17, 2020, 12 pages.

* cited by examiner

FIGURE 2

| Arm-1 | WD/SW | + Pioglitazone, Gavage |
|---|---|---|
| Arm-2 | WD/SW | + Larazotide, Vehicle (VC), Bottle |
| Arm-3 | WD/SW | + Larazotide, Vehicle (VC), Gavage |
| Arm-4 | WD/SW | + Larazotide, Low-Dose (LD), Bottle |
| Arm-5 | WD/SW | + Larazotide, High-Dose (HD), Bottle |
| Arm-6 | WD/SW | + Larazotide, Low-Dose (LD), Gavage |
| Arm-7 | WD/SW | + Larazotide, High-Dose (HD), Gavage |
| Arm-8 | ND/NW | |

LARAZOTIDE FORMULATIONS

CROSS-REFERENCE TO RELATED APPLICATIONS

This application claims the benefit of U.S. Provisional Application No. 63/009,768, filed on Apr. 14, 2020, and 62/888,052, filed on Aug. 16, 2019, the entire contents of which are hereby incorporated by reference.

FIELD OF THE INVENTION

The present invention provides compositions, formulations and methods for treating diseases and disorders of the small bowel, such as but not limited to fatty liver disease.

BACKGROUND

The intestinal epithelium is the layer of cells that forms the luminal surface of the small and large intestines of the gastrointestinal (GI) tract, and represents the largest interface (more than 400 $m^2$) between the external environment and the internal milieu. The intestinal epithelium has two important functions: absorbing nutrients and providing a barrier against harmful environmental substances such as bacteria, viruses, toxins, and food allergens.

The barrier properties of the intestinal epithelium are regulated by specialized plasma membrane structures known as tight junctions. Alterations in tight junctions can result in disruptions of the intestinal barrier functions and increased intestinal permeability. An intact intestinal barrier prevents the permeation of pathogens, antigens, endotoxins, and other proinflammatory substances into the body, whereas intestinal disintegrity allows their entry, which may trigger local or systemic inflammation and disease.

For example, nonalcoholic steatohepatitis (NASH) is a severe disease of the liver caused by inflammation and a buildup of fat in the organ. In the United States, NASH affects up to approximately 2-5% of the population. An additional 10-30% of Americans have fat in their livers, but no inflammation or liver damage, a condition called NAFLD or "fatty liver." The underlying cause of NASH is unclear, but it most often occurs in persons who are middle-aged and overweight or obese. Lipotoxicity and the gut-liver axis (with its two components) are main contributors in the pathogenesis of NASH. Perturbations in the epithelial lining of the intestine and disruption of barrier integrity cause an increase in permeability of the epithelium and passage of unwanted toxins and also cause antigenic components to "cross-talk" to the liver via the circulation, which causes inflammation and damage to hepatocytes. Dysbiosis of the microbiota and alterations of intestinal immunity leads to increased translocation of bacteria and bacterial products into the systemic circulation. Consequently, bacteria or bacterial products are able to reach the liver through the portal vein.

In the liver, conserved motifs/structures of bacteria and bacterial products (PAMPs) lead to hepatic steatosis, inflammation, and fibrosis. Chronic liver diseases, including NAFLD/NASH, may be associated with perturbations in the epithelial lining of the gut and disruption of barrier integrity, causing a normal intestine to become more permeable. This "leaky gut" can allow passage of unwanted toxins and antigenic components to "cross-talk" to the liver via the blood circulation causing inflammation and damage to hepatocytes and other organs or cells. Complications can lead to liver fibrosis and then to cirrhosis and then to liver cancer. These chronic liver diseases represent the main reasons for liver transplantation and primary liver cancer.

Accordingly, there is a need for effective treatments for intestinal barrier dysfunction for treating, ameliorating, and slowing progression of disease, including NAFLD and NASH.

SUMMARY OF THE INVENTION

The present invention in various aspects and embodiments provides pharmaceutical compositions for delivering larazotide or a derivative thereof, or salts thereof, to the small or large intestine, including to the small bowel for therapy of fatty liver diseases, such as NASH. In some embodiments, the composition provides a sustained release of the larazotide or derivative to the jejunum and ileum of a human subject. In other aspects and embodiments, the invention provides for treatment of inflammatory and fatty liver disease with the compositions disclosed herein.

In various embodiments, the larazotide or derivative is administered in a sustained release or controlled release or modified release formulation. The sustained release or controlled release or modified release formulation improves dose response to the active agent. For example, the formulation may deliver and/or functionally release from 0.25 to about 5 mg of larazotide or derivative. In various embodiments, the sustained release or controlled release or modified release formulation delivers at least about 0.25 mg, or at least about 0.5 mg, or at least about 1 mg, or at least 2 mg of larazotide or derivative.

The sustained or controlled release or modified release formulation may functionally release peptide over the course of at least about 2 hours, or over the course of at least about 2.5 hours, or over the course of at least about 3 hours, or over the course of at least about 4 hours, or over the course of at least about 5 hours. In some embodiments, the sustained or controlled release composition begins to release peptide starting within about 10 to about 30 minutes of exposure to simulated intestinal fluid, with release of peptide continuing for at least about 180 minutes, or at least about 210 minutes, or at least about 240 minutes, or at least about 280 minutes of exposure to simulated intestinal fluid. Release profiles can be prepared, for example, using compositions with different enteric polymer coats and/or different thicknesses of the polymer coats. In some embodiments, the invention provides a composition comprising an effective amount of a peptide that is larazotide or a larazotide derivative, or salt thereof, contained within a biodegradable or erodible polymer matrix, which further comprises an enteric coating.

In some embodiments, the beads further comprise an enteric coating that is substantially resistant to dissolution in simulated gastric fluid. The composition remains essentially intact, or may be essentially insoluble, in gastric fluid. The stability of a gastric-resistant coating can be pH dependent. For example, the enteric coating may prevent substantial release of the peptide in simulated gastric fluid as well as simulated intestinal fluid having a pH of about 5.5. In some embodiments, the matrix provides for the sustained release of the peptide in simulated intestinal fluid having a pH of about 6 or more, such as from about 6.5 to about 7.0. Thus, the enteric coating is stable in simulated gastric fluid but unstable in simulated intestinal fluid having a pH above about 6.0. The enteric coating in such embodiments does not substantially release peptide in the duodenum, but delays release until the composition enters the jejunum, and thereafter providing a sustained release in the jejunum and ileum.

In some embodiments, the composition is a capsule for oral delivery comprising a population of beads, the population of beads comprising an effective amount of larazotide or larazotide derivative or salt thereof contained within an erodible polymer matrix, the beads further comprising an enteric coating comprising a co-polymer of methyl acrylate, methyl methacrylate, and methacrylic acid. The ratio of free carbonyl groups to ester groups in the co-polymer may be about 1:10 (e.g., EUDRAGIT F30D). In such embodiments, the enteric coating may be from about 20% to about 30% of the total weight of the composition. In some embodiments, the erodible matrix comprises microcrystalline cellulose. In some embodiments, the composition provides for less than about 15% release of peptide after about 2 hours in simulated gastric fluid. Further, the composition provides for less than about 25% release of peptide after about 2 hours in simulated intestinal fluid having a pH of about 5.5. In various embodiments, the composition releases at least about 40% but no more than about 80% of peptide after about 2 hours in simulated intestinal fluid having a pH of about 7.0. In various embodiments, 100% release in simulated intestinal fluid having a pH of about 7 is not reached until at least three hours, or in some embodiments, at least about 3.5 or at least about four hours.

In still other aspects, the present invention provides methods for treating disorders, conditions, and/or diseases of the small bowel. Such small bowel disorders are often associated with intestinal barrier dysfunction and increased intestinal permeability. For example, intestinal barrier dysfunction and increased intestinal permeability can be linked to various inflammatory liver diseases, including nonalcoholic fatty liver disease (NAFLD), nonalcoholic steatohepatitis (NASH), and cirrhosis (e.g., alcohol cirrhosis). In some embodiments, the subject has one or more conditions associated with the liver disease, such as kidney disease (e.g., chronic kidney disease), viral hepatitis, and diabetes, hypertriglyceridemia, and/or insulin resistance.

In some embodiments, the patient may receive adjunct therapy, which in some embodiments is synergistic with larazotide treatment. In some embodiments, the invention involves administering a regimen of larazotide (or a derivative of larazotide) to a subject, resulting in improved glycemic control. In various embodiments, the regimen of larazotide improves the effectiveness of conventional pharmaceutical interventions, such as metformin, basal insulin, GLP-1 receptor agonists (e.g., liraglutide), inhibitor of the sodium glucose co-transporter-2 (SGLT-2), gastric inhibitory peptide (GIP), sulphonylurea, pPAR-gamma agonists, obeticholic acid, among others. In accordance with the invention, the larazotide regimen prevents complications of hyperglycemia, including cardiovascular complications and damage to organs.

In another aspect, the present invention provides compositions and methods for treating a patient having cancer, as well as methods for potentiating cancer immunotherapy. The compositions described herein can improve cancer immunotherapy treatment by reducing epithelial permeability of the small and/or large bowel. See PCT/US2019/022885, which is hereby incorporated by reference in its entirety. Furthermore, the cancer can be any cancer treatable by immunotherapy, including immune checkpoint inhibitor therapy, including primary cancers, metastatic cancers, and hematological cancers. In some embodiments, a pharmaceutical composition comprising larazotide is administered to potentiate the efficacy of the immunotherapy (e.g., immune checkpoint inhibitor therapy), including for subjects that showed no response or only a partial response to prior treatment with an immune checkpoint inhibitor therapy.

Other aspects and embodiments of the invention will be apparent from the following detailed description.

DESCRIPTION OF THE FIGURES

FIG. 2 depicts the study design for administration of larazotide acetate to mice subsisting on a Western diet with compromised gut integrity. 8 groups of mice were placed on the Western diet for 16 weeks and administered larazotide, pioglitazone comparator or vehicle from 8 to 16 weeks. Serum dextran concentrations were measured at baseline and at the end of the study.

DETAILED DESCRIPTION

The present invention in various aspects and embodiments provides pharmaceutical compositions for delivering larazotide or a derivative thereof, or salts thereof, to the small and/or large bowel for therapy, including for fatty liver disease such as NASH, as well as for treatment of cancer via potentiation of an immunotherapy. In some embodiments, the composition provides a sustained release of the larazotide or derivative to the jejunum and ileum of a human subject. In other aspects and embodiments, the invention provides for treatment of inflammatory and fatty liver disease with the compositions disclosed herein. In other aspects and embodiments, the invention provides for treatment of a patient having cancer, as well as methods for potentiating an immune checkpoint inhibitor therapy, with the compositions disclosed herein.

Larazotide is a peptide agent that promotes tight junction integrity in the gastrointestinal tract (GI). Larazotide has the amino acid sequence: Gly Gly Val Leu Val Gln Pro Gly (SEQ ID NO:1), and can be formulated for targeted release in portions of the GI. Larazotide has been shown in clinical trials to exhibit benefit at reducing celiac disease symptoms, particularly at lower doses (e.g., 0.5 mg dose). See US 2016/0022760, which is hereby incorporated by reference in its entirety. Higher doses (e.g., 1 mg and 2 mg doses) showed an attenuation of activity, or no activity at all. It is believed that an exopeptidase, such as aminopeptidase, located within the brush borders of the lumen surface may create larazotide-derived fragments, including fragments missing N-terminal glycine residues. For example, the fragments GVLVQPG (SEQ ID NO:2) and VLVQPG (SEQ ID NO:3) are inactive as tight junction regulators. Moreover, when these two fragments are mixed with full length larazotide, activity is completely abolished. Local buildup of these inactive larazotide fragments (due to excessive larazotide) may in fact compete and block function of the peptide. This would explain clinical observations that low doses of larazotide work best by avoiding the reservoir of competing inactive fragments. Thus, in some embodiments, controlled release or sustained release or modified release formulations are employed to increase effectiveness of larazotide or derivative.

Figure 10:
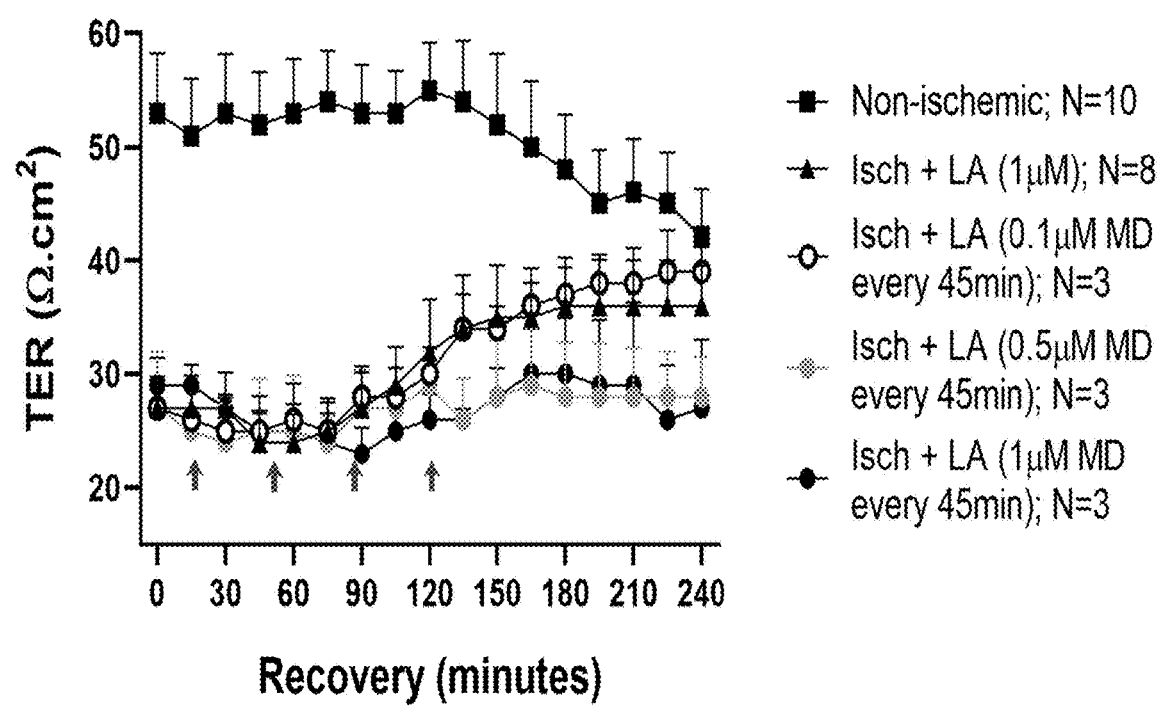
FIG. 10 depicts the results of an ex-vivo ischemic jejunum model measuring TER (transepithelial resistance) at various concentrations (0.1 µM, 0.5 µM, or 1 µM) of larazotide that were administered every 45 minutes in fractional doses.

Microdosing of the larazotide active agent can prevent local buildup of inactive fragments (FIG. 10). For example, a formulation releasing small amounts of larazotide over an extended period of time improves the effect of the active agent. It is believed that a sustained release of larazotide would be more effective than a larger release of active agent around the same location.

In some embodiments, the active agent is larazotide. In other embodiments, the active agent is a larazotide derivative, for example, having one or more amino acid modifications, such as amino acid substitutions, deletions, and/or insertions. For example, the derivative may have 1, 2, 3, or 4 amino acid modifications independently selected from amino acid deletions, insertions, and/or substitutions with respect to SEQ ID NO:1. Exemplary larazotide derivatives are described in U.S. Pat. Nos. 8,785,374, 8,957,032, and 9,279,807, which are hereby incorporated by reference in their entirety. Additional larazotide derivatives are disclosed in PCT/US2019/19350, which is hereby incorporated by reference.

For example, in some embodiments, a larazotide derivative is administered that exhibits resistance to exopeptidases, such as aminopeptidases, thus avoiding substantial accumulation of inactive peptide fragments. Exemplary modifications include amino acid substitutions at the N- and/or C— terminus to reduce exopeptidase digestion, extension of the N- and/or C— termini to delay exopeptidase digestion of the functional peptide, incorporation of D amino acids, as well as cyclization. Exemplary larazotide derivatives are disclosed in PCT/US2019/19350, which is hereby incorporated by reference in its entirety.

In various embodiments, the peptide has at least one, at least two, at least three, at least four, at least five, at least six, at least seven, or at least eight D-amino acids. In an embodiment, each amino acid of the Larazotide derivative (other than Gly) is a D-amino acid, and is optionally a retro-inverso peptide. A retro-inverso peptide contains the inverse amino acid sequence (e.g., GPQVLVGG), with all non-glycine amino acids present as D-amino acids. Retro-inverso peptides maintain side chain topology similar to that of the original L-amino acid peptide, and render the peptide more resistant to proteolytic degradation. In some embodiments, the N-terminal Gly of the retro-inverso peptide is substituted with Ala, Leu, Ile, Val, or Allylglycine. In these or other embodiments, one or both of the C-terminal Gly residues of the retro inverso peptide is/are substituted with an amino acid independently selected from Ala, Leu, Ile, Val, or Allylglycine.

In other embodiments, the peptide having the amino acid sequence of SEQ ID NO:1 has one or two D-amino acids at the N- and optionally the C-terminus, with all other amino acids in the L configuration. For example, the peptide having the amino acid sequence of SEQ ID NO: 1 has L-Pro replaced with D-Pro and all other amino acids in the L configuration. In these embodiments, the N- and/or C-terminus are substituted or extended such that the peptide does not have a glycine at the terminus (Gly does not have D- and L-configurations). In some embodiments, the terminal Gly residues are replaced with D-Ala. The term "larazotide" or "larazotide treatment" refers to treatment with larazotide or a derivative that promotes tight junction integrity.

In some embodiments, the larazotide derivative is d-larazotide, that is, having a D-amino acid at each position that is not Gly. D-larazotide provides advantages in dosing and/or efficacy as compared to larazotide.

Larazotide or derivative may be administered in any suitable form, including as a salt. For example, larazotide or derivative may be administered as an acetate salt. Salts of larazotide, including the acetate salt and hydrochloride salt, are described in US 2013/0281384, which is hereby incorporated by reference in its entirety. Alternative salts may be employed, including any pharmaceutically acceptable salt of the peptide such as those listed in Journal of Pharmaceutical Science, 66, 2-19 (1977) and The Handbook of Pharmaceutical Salts; Properties, Selection, and Use. P. H. Stahl and C. G. Wermuth (eds.), Verlag, Zurich (Switzerland) 2002, which are hereby incorporated by reference in their entirety.

In various embodiments, the larazotide or derivative is administered in a sustained release or controlled release formulation. The sustained release or controlled release or modified release formulation avoids an inverse dosing response, where the sustained release or controlled release or modified release formulation does not overwhelm larazotide receptors at the target site of delivery with inactive peptide. For example, the formulation may deliver and/or functionally release from 0.25 to about 5 mg of larazotide or derivative, or from about 0.25 to about 4 mg of larazotide or derivative, or from about 0.25 to about 3 mg of larazotide or derivative, or from about 0.25 to about 2 mg of larazotide or derivative, or from about 0.25 to about 1 mg of larazotide or derivative. In various embodiments, the sustained release or controlled release or modified release formulation delivers at least about 0.25 mg, or at least about 0.5 mg, or at least about 1 mg, or at least 2 mg of larazotide or derivative. For example, the formulation may contain from about 1 mg to about 5 mg of larazotide or derivative, or about 1 mg to about 3 mg of larazotide or derivative. In some embodiments, the formulation may contain from about 0.25 mg to about 1 mg of larazotide or derivative, or about 0.5 mg to about 2 mg of larazotide or derivative. As used herein, the term "about" include ±10% of the associated numerical value.

The sustained or controlled release or modified release formulation may release peptide over the course of at least about 2 hours, or over the course of at least about 2.5 hours, or over the course of at least about 3 hours, or over the course of at least about 4 hours, or over the course of at least about 5 hours. In some embodiments, the sustained or controlled release composition (e.g., comprising peptide-containing particles, gels, emulsions, or biodegradable or erodible matrix) begins to release peptide starting within about 10 to about 30 minutes of exposure to simulated intestinal fluid, with release of peptide continuing for at least about 180 minutes, or at least about 210 minutes, or at least about 240 minutes, or at least about 280 minutes of exposure to simulated intestinal fluid. Release profiles can be prepared, for example, using compositions with different enteric polymer coats and/or different thicknesses of the polymer coats.

In some embodiments, the invention provides a composition comprising an effective amount of a peptide that is larazotide or a larazotide derivative, or salt thereof, contained within a biodegradable or erodible polymer matrix. The matrix provides for sustained release of the peptide in simulated intestinal fluid for at least about 120 minutes. In some embodiments, the matrix provides for a sustained release of the peptide in simulated intestinal fluid for at least about 180 minutes, or for at least about 210 minutes, or for at least about 240 minutes. The simulated intestinal fluid may have a pH of at least about 6.0, or at least about 6.2, or at least about 6.5. In some embodiments, the simulated intestinal fluid has a pH of about 7.

In some embodiments, the beads further comprise an enteric coating that is substantially resistant to dissolution in simulated gastric fluid. The composition remains essentially intact, or may be essentially insoluble, in gastric fluid. The stability of a gastric-resistant coating (referred to herein as an "enteric coating") can be pH dependent. Delayed-release coatings that are pH dependent will be substantially stable in acidic environments (e.g., pH of about 5.5 or less), and substantially unstable in near neutral to alkaline environments (e.g., pH greater than about 6.0). For example, an enteric coating can be employed that will essentially disintegrate or dissolve in near neutral to alkaline environments such as are found in the small intestine, such as the jejunum and ileum. Examples of simulated gastric fluid and simulated intestinal fluid include, but are not limited to, those disclosed in the 2005 Pharmacopeia 23NF/28USP in Test Solutions and/or other simulated gastric fluids and simulated intestinal fluids known to those of skill in the art, for example, simulated gastric fluid and/or intestinal fluid prepared without enzymes.

For example, the enteric coating may prevent substantial release of the peptide in simulated gastric fluid as well as simulated intestinal fluid having a pH of about 5.5. In some embodiments, the matrix provides for the sustained release of the peptide in simulated intestinal fluid having a pH of about 6 or more, such as from about 6.5 to about 7.0. Thus, the enteric coating is stable in simulated gastric fluid but unstable in simulated intestinal fluid having a pH above about 6.0. The enteric coating in such embodiments does not substantially release peptide in the duodenum, but delays release until the composition enters the jejunum, and thereafter providing a sustained release in the jejunum and ileum. The composition does not substantially deliver peptide to the colon.

Alternatively, the stability of the delayed-release coating can be enzyme-dependent. Delayed-release coatings that are enzyme dependent will be substantially stable in fluid that does not contain a particular enzyme and substantially unstable in fluid containing the enzyme. The coating will essentially disintegrate or dissolve in fluid containing the appropriate enzyme. Enzyme-dependent control can be brought about, for example, by using materials that release the active ingredient only on exposure to enzymes in the intestine, such as galactomannans.

Various types of enteric coatings for delayed yet substantial delivery of active agents to the GI tract are known. In some embodiments, the sustained-release composition includes an enteric agent that is substantially stable in acidic environments and substantially unstable in near neutral to alkaline environments. In an embodiment, the sustained-release coating contains an enteric agent that is substantially stable in gastric fluid. The enteric agent can be selected from, for example, solutions or dispersions of methacrylic acid copolymers, cellulose acetate phthalate, hydroxypropylmethyl cellulose phthalate, polyvinyl acetate phthalate, carboxymethylethylcellulose, and EUDRAGIT®-type polymer (poly(methacrylic acid, methylmethacrylate), hydroxypropyl methylcellulose acetate succinate, cellulose acetate trimellitate, shellac or other suitable enteric coating polymers. The EUDRAGIT®-type polymer include, for example, EUDRAGIT® FS 30D, L 30 D-55, L 100-55, L 100, L 12,5, L 12,5 P, RL 30 D, RL PO, RL 100, RL 12,5, RS 30 D, RS PO, RS 100, RS 12,5, NE 30 D, NE 40 D, NM 30 D, S 100, S 12,5, and S 12,5 P. In some embodiments, one or more of EUDRAGIT® FS 30D, L 30 D-55, L 100-55, L 100, L 12,5, L 12,5 P RL 30 D, RL PO, RL 100, RL 12,5, RS 30 D, RS PO, RS 100, RS 12,5, NE 30 D, NE 40 D, NM 30 D, S 100, S 12,5 ands 12,5 P is used. The enteric agent may be a combination of the foregoing solutions or dispersions. In some embodiments, the enteric agent is EUDRAGIT F30D, which comprises a co-polymer of methyl acrylate, methyl methacrylate, and methacrylic acid. The co-polymer has a ratio of free carbonyl groups to ester groups of about 1:10.

In another embodiment, the sustained-release coating may degrade as a function of time when in aqueous solution without regard to the pH and/or presence of enzymes in the solution. Such a coating may comprise a water insoluble polymer. Its solubility in aqueous solution is therefore independent of the pH. The term "pH independent" as used herein means that the water permeability of the polymer and its ability to release pharmaceutical ingredients is not a function of pH and/or is only very slightly dependent on pH. Such coatings may be used to prepare, for example, sustained release formulations. Suitable water insoluble polymers include pharmaceutically acceptable non-toxic polymers that are substantially insoluble in aqueous media, e.g., water, independent of the pH of the solution. Suitable polymers include, but are not limited to, cellulose ethers, cellulose esters, or cellulose ether-esters, i.e., a cellulose derivative in which some of the hydroxy groups on the cellulose skeleton are substituted with alkyl groups and some are modified with alkanoyl groups. Examples include ethyl cellulose, acetyl cellulose, nitrocellulose, and the like. Other examples of insoluble polymers include, but are not limited to, lacquer, and acrylic and/or methacrylic ester polymers, polymers or copolymers of acrylate or methacrylate having a low quaternary ammonium content, or mixture thereof and the like. Other examples of insoluble polymers include EUDRAGIT RS®, EUDRAGIT RL®, EUDRAGIT NE®, polyvinyl esters, polyvinyl acetals, polyacrylic acid esters, butadiene styrene copolymers, and the like.

In some embodiments, the composition involves a coated tablet, or coated beads or granules, having a delayed-release profile as described in, for example, U.S. Pat. No. 8,168,594, the entire contents of which are hereby incorporated by reference. An exemplary enteric coating comprises a copolymer of acrylate and methacrylate, which is a 1:1 copolymer in some embodiments. Other fillers, binder, and plasticizers, including for seal coats or top coats, are described in U.S. Pat. No. 8,168,594, which is hereby incorporated by reference.

For example, compositions can include one or more separating layers. The separating layer separates the core tablet or particle from the delayed-release coating. The separating layer can be applied to the core by coating or layering procedures typically used with coating equipment such as a coating pan, coating granulator or in a fluidized bed apparatus using water and/or organic solvents for the coating process. As an alternative, the separating layer can be applied to the core material by using a powder coating technique. The materials for separating layers are pharmaceutically acceptable compounds such as, for instance, sugar, polyethylene glycol, polyvinylpyrrolidone, polyvinyl alcohol, polyvinyl acetate, hydroxypropyl cellulose, methylcellulose, ethylcellulose, hydroxypropyl methylcellulose, carboxymethylcellulose sodium and others, used alone or in mixtures. Additives such as plasticizers, colorants, pigments, fillers, anti-tacking and anti-static agents, such as for instance magnesium stearate, titanium dioxide, talc and other additives can also be included in the separating layer.

An enteric coating composition can be dispersed or dissolved in either water or in a suitable organic solvent and applied to the core particle by methods well known to those of ordinary skill in the art. One or more delayed-release coatings can be applied to the coated core particle.

The enteric coating or other coats can include one or more inert processing aids, including but not limited to talc, silicon dioxide, magnesium stearate and the like. The enteric coating compositions can also contain pharmaceutically acceptable plasticizers to obtain the desired mechanical properties such as flexibility and hardness. Such plasticizers include, but are not limited to, triacetin, citric acid esters, phthalic acid esters, dibutyl sebacate, cetyl alcohol, polyethylene glycols, polysorbates or other plasticizers.

For example, in some embodiments, the coated particles or tablets can be further covered with an overcoat layer. The overcoat materials are pharmaceutically acceptable compounds such as sugar, polyethylene glycol, polyvinylpyrrolidone, polyvinyl alcohol, polyvinyl acetate, hydroxypropyl cellulose, methylcellulose, ethylcellulose, hydroxypropyl methylcellulose, carboxymethylcellulose sodium and others, used alone or in mixtures. The overcoat materials can prevent potential agglomeration of particles coated with the enteric coating, protect the coating from cracking during the compaction process or enhance the tableting process.

Thus, in some embodiments, the matrix comprises one or more binders, fillers, or plasticizers. Such components include one or more of cellulose or cellulose derivative, fatty acid salt, or synthetic polymer. For example, the binder, filler, or plasticizer may comprise a synthetic polymer, and the polymer is optionally a co-polymer of vinyl pyrrolidine and vinyl acetate. Alternatively, the binder, filler, or plasticizer comprises a cellulose derivative, which optionally comprises one or more of ethyl cellulose, hydroxypropylmethyl cellulose, and carboxymethyl cellulose. In some embodiments, the binder, filler, or plasticizer includes a fatty acid salt, optionally selected from a C8 to C18 fatty acid salt, which is optionally a salt of stearic acid (e.g., magnesium stearate). In some embodiments, the enteric coating comprises a plasticizer, which is optionally triethyl citrate.

The oral dosage composition can be in the form of a capsule comprising granules or beads, or may be an enteric-coated tablet, or other form. In some embodiments, the composition comprises a population of beads or granules containing the matrix and an enteric coating, which may be contained within a capsule. For example, in some embodiments, the beads comprise an enteric coating comprising a co-polymer of methyl acrylate, methyl methacrylate, and methacrylic acid, and which may optionally have a ratio of free carbonyl groups to ester groups of about 1:10. Such an enteric coating may be from about 15% to about 40% by weight of the composition. In some embodiments, the enteric coating is from about 20% to about 30% by weight of the composition, or from about 20% to about 25% by weight of the composition.

The polymer matrix can be selected such that it degrades or erodes in a substantially pH independent manner. In other embodiments, the polymer matrix degrades or erodes in a pH dependent manner. An exemplary polymer matrix comprises a polysaccharide matrix, such as a matrix comprising one or more of cellulose, chitin, chitosan, alginate, amylose, pectin, callose, laminarin, chrysolaminarin, xylan, arabinoxylan, mannan, fucoidan, galactomannan, xanthan gum, dextran, welan gum, gellan gum, diutan gum, pullulan, hyaluronic acid, and derivatives thereof. Derivatives of cellulose, for example, include alkyl, hydroxyl, and carboxylated derivatives. In some embodiments, the matrix comprises microcrystalline cellulose. In still other embodiments, the matrix comprises various biodegradable synthetic polymer known in the art.

In some embodiments, the composition is a capsule for oral delivery comprising a population of beads, the population of beads comprising from 0.25 to 2 mg of larazotide or larazotide derivative or salt thereof contained within an erodible polymer matrix, the beads further comprising an enteric coating comprising a co-polymer of methyl acrylate, methyl methacrylate, and methacrylic acid. The ratio of free carbonyl groups to ester groups in the co-polymer may be about 1:10 (e.g., EUDRAGIT F30D). In such embodiments, the enteric coating is from about 20% to about 30% of the total weight of the composition. In some embodiments, the erodible matrix comprises microcrystalline cellulose. The composition may further comprise a seal coat or top coat.

In some embodiments, the composition provides for less than about 15% release of peptide after about 2 hours in simulated gastric fluid. Further, the composition provides for less than about 25% release of peptide after about 2 hours in simulated intestinal fluid having a pH of about 5.5. In various embodiments, the composition releases at least about 40% but no more than about 80% of peptide after about 2 hours in simulated intestinal fluid having a pH of about 7.0. In various embodiments, 100% release in simulated intestinal fluid having a pH of about 7 is not reached until at least three hours, or in some embodiments, at least about 3.5 or at least about four hours.

In still other aspects, the present invention provides methods for treating disorders, conditions, and/or diseases of the small bowel. Such small bowel disorders are often associated with intestinal barrier dysfunction and increased intestinal permeability. For example, intestinal barrier dysfunction and increased intestinal permeability can be linked to various inflammatory liver diseases, including nonalcoholic fatty liver disease (NAFLD), nonalcoholic steatohepatitis (NASH), and cirrhosis (e.g., alcohol cirrhosis). In some embodiments, the present invention provides methods for preventing and/or treating celiac disease.

In accordance with certain embodiments, larazotide or derivative is administered one or more times daily to promote GI tight junction integrity. For example, larazotide or derivative may be administered once daily, about two times daily, or about three times daily, or more. In various embodiments, the regimen of larazotide or derivative is administered for a prolonged period. In some embodiments, the regimen of larazotide or derivative is administered for at least about 1 month, at least about 2 months, at least about 4 months, and at least about 8 months. For example, the regimen of larazotide or derivative is administered for at least about 6 months. In some embodiments, treatment is continuous to delay or prevent disease progression.

In some embodiments, the subject has a fatty liver disease including, but not limited to NAFLD, NASH, alcoholic steatohepatitis (ASH), or a fatty liver disease resulting from hepatitis, obesity, diabetes, insulin resistance, hypertriglyceridemia, chronic kidney disease, abetalipoproteinemia, glycogen storage disease, Weber-Christian disease, Wolmans disease, acute fatty liver of pregnancy, and lipodystrophy. In some embodiments, improvements in intestinal barrier function limit the amount of toxins such as LPS that enter circulation and which can ultimately exacerbate disease or promote disease progression. In some embodiments, the subject has NASH.

In some embodiments, the present invention provides for the treatment of a patient with NAFLD. NAFLD represents a spectrum of disease occurring in the absence of alcohol abuse. NAFLD is characterized by the presence of steatosis (fat in the liver) and may represent a hepatic manifestation of the metabolic syndrome (including obesity, diabetes and hypertriglyceridemia). The severity of NAFLD ranges from the relatively benign isolated predominantly macrovesicular steatosis (i.e., nonalcoholic fatty liver or NAFL) to non-alcoholic steatohepatitis (NASH). NASH is characterized by the histologic presence of steatosis, cytological ballooning, scattered inflammation and pericellular fibrosis. Hepatic fibrosis resulting from NASH may progress to cirrhosis of the liver or liver failure, and in some instances may lead to hepatocellular carcinoma. In some embodiments, methods of the invention reduce or ameliorate one or more symptoms of NAFLD or NASH, and may improve or preserve liver function. In some embodiments, method of the invention prevents or slows the progression of NAFLD or NASH.

In some embodiments, the invention provides a method of treating or preventing inflammatory liver disease in a subject. The method comprises administering to a subject in need thereof the composition disclosed herein. In some embodiments, the subject has a fatty liver disease. In some embodiments, the subject has an inflammatory liver disease selected from non-alcoholic steatohepatitis (NASH) or non-alcoholic fatty acid liver disease (NAFLD). In still other embodiments, the subject has alcoholic steatohepatitis (ASH).

In some embodiments, the present invention provides for the treatment of a patient with hepatitis. In exemplary embodiments, the hepatitis may be caused by viruses, alcohol, drugs, and the like. In an embodiment, the present invention provides for the treatment of a patient with hepatitis A, hepatitis B, hepatitis C, hepatitis D, or hepatitis E. In another embodiment, the present invention provides for the treatment of alcoholic hepatitis. In a further embodiment, the present invention provides for the treatment of autoimmune hepatitis. Symptoms of hepatitis include fatigue, flu-like symptoms, dark urine, pale stool, abdominal pain, loss of appetite, unexplained weight loss, and jaundice. Chronic hepatitis is also associated with cirrhosis and hepatocellular carcinoma. In various embodiments, methods of the invention reduce, ameliorate, or eliminate one or more symptoms of hepatitis.

In some embodiments, the subject has one or more conditions associated with the liver disease, such as kidney disease (e.g., chronic kidney disease), viral hepatitis, diabetes, hypertriglyceridemia, and/or insulin resistance.

In some embodiments, the patient may receive adjunct therapy, which in some embodiments is synergistic with larazotide treatment. In some embodiments, the invention involves administering a regimen of larazotide (or a derivative of larazotide) to a subject, resulting in improved glycemic control. In various embodiments, the regimen of larazotide improves the effectiveness of conventional pharmaceutical interventions, such as metformin, basal insulin, GLP-1 receptor agonists (e.g., liraglutide), gastric inhibitory peptide (GIP), sulphonylurea, pPAR-gamma agonists, obeticholic acid, among others. In accordance with the invention, the larazotide regimen prevents complications of hyperglycemia, including cardiovascular complications and damage to organs. Without wishing to be bound by any one theory, it is proposed that uncontrolled hyperglycemia can result in or be associated with intestinal barrier dysfunction and development of fatty liver disease. These dysfunctions reduce the efficacy of traditional pharmaceutical interventions for hyperglycemia and diabetes, and allows for the diffusion of microbes and toxins (e.g., lipopolysaccharides or LPS) from the lumen of the intestine into the intestinal lamina propria and systemic circulation, which in turn cause systemic infection or damage to tissues and organs. Further, in subjects with hyperglycemia-induced intestinal barrier dysfunction, glucose may leak into the circulation via the disrupted epithelial tight junctions, which may impact the efficacy of pharmaceutical agents prescribed for glycemic control.

In still other embodiments, the compositions described herein are administered to patients exhibiting symptoms of intestinal permeability, including but not limited to, patients having celiac disease, inflammatory bowel syndrome, Crohn's disease, chronic kidney disease, as well as various autoimmune conditions such as diabetes mellitus.

In other aspects, the present invention provides methods for treating a subject having cancer, as well as methods for potentiating immunotherapy. Methods of treating cancer and/or potentiating an immune checkpoint inhibitor therapy via administration of larazotide, or derivatives thereof, to a subject in need are described in International Application No. PCT/US19/22885, filed on Mar. 19, 2019, the entire contents of which are hereby incorporated by reference. Without wishing to be bound by theory, it is believed that maintenance of a healthy gut mucosa (e.g., via administration of larazotide, or derivatives therof) can lead to improved efficacy of immunotherapy, including checkpoint inhibitor therapy, lymphocyte stimulatory therapy, or T cell therapy (e.g., CAR-T cell therapy).

In some embodiments, such methods for treating cancer and/or potentiating an immune checkpoint inhibitor therapy include treating subjects undergoing checkpoint inhibitor therapy, and/or subjects scheduled to undergo immune checkpoint inhibitor therapy. In some embodiments, the subject showed no response or only a partial response to prior treatment with an immune checkpoint inhibitor therapy. In some embodiments, the subject did not achieve at least stable disease through prior treatment with an immune checkpoint inhibitor therapy. In some embodiments, the prior immune checkpoint inhibitor therapy was a PD-1 blockade therapy (e.g., anti-PD-1 or anti-PD-L1).

In some embodiments, the one or more immune checkpoint inhibitors are selected from an inhibitor of: Programmed Death-Ligand 1 (PD-L1, also known as B7-H1, CD274), Programmed Death 1 (PD-1), CTLA-4, PD-L2 (B7-DC, CD273), LAG3, TIM3, 2B4, A2aR, B7H1, B7H3, B7H4, BTLA, CD2, CD27, CD28, CD30, CD40, CD70, CD80, CD86, CDI37, CDI60, CD226, CD276, DR3, GALS, GITR, HAVCR2, HVEM, IDOL ID02, ICOS (inducible T cell costimulator), KIR, LAIRI, LIGHT, MARCO (macrophage receptor with collagenous structure), PS (phosphatidylserine), OX-40, SLAM, TIGHT, VISTA, and VTCNI. In some embodiments, the immune checkpoint inhibitor is an inhibitor of PD-1 or PD-L 1. In some embodiments, the immune checkpoint inhibitor is selected from ipilimumab, tremelimumab, pembrolizumab and nivolumab.

In some embodiments, the immune checkpoint inhibitor is a monoclonal antibody, such as anti-CTLA-4, anti-PD-1, or anti-PD-L1 and/or PD-L2 agent (e.g. YERVOY, OPDIVO, or KEYTRUDA, or comparable agents thereto). In various embodiments, these agents can be administered in a plurality of doses, such as from 4 to 12 doses or from 4 to 8 doses, which can be administered over a 1-4 month period of time in some embodiments (e.g., 1 or 2 months in some embodiments).

In some embodiments, the immunotherapy comprises administering an agonist of a lymphocyte co-stimulatory molecule, such as OX40 or Ox40L, CD28, or 4-1BB.

In some embodiments, compositions described herein comprising or releasing larazotide or a derivative thereof are administered in a regimen of at least once per day. In some embodiments, the compositions are administered in a regimen including administration from 1 to 5 times daily, such as from 1 to 3 times daily. In some embodiments, the regimen is initiated before immunotherapy (e.g., checkpoint inhibitor therapy), for example, at least one week prior to initiation of immunotherapy (e.g., checkpoint inhibitor therapy), or in some embodiments, at least 2 weeks, at least 3 weeks, at least 4 weeks (about 1 month) prior to initiation of immunotherapy (e.g., checkpoint inhibitor therapy). In these or other embodiments, the regimen is continued throughout the duration of immunotherapy (e.g., checkpoint inhibitor therapy), and optionally for a period of time thereafter (e.g., at least one month or more after an immunotherapy or checkpoint inhibitor therapy regimen).

In various embodiments, administration of a composition comprising larazotide or derivative increases or restores the efficacy of immune checkpoint inhibitor therapy. For example, in some embodiments, the subject having cancer was previously unresponsive to, or had become resistant to, an immune checkpoint inhibitor. In some embodiments, for example, the cancer is refractory or insufficiently responsive to an immunotherapy, such as anti-CTLA-4, anti-PD-1, or anti-PD-L1 and/or PD-L2 agent. In some embodiments, the cancer subject has progressed after or during treatment with an anti-CTLA-4, anti-PD-1, or anti-PD-L1 and/or PD-L2 agent, including for example, one or more of ipilimumab, tremelimumab, pembrolizumab and nivolumab, or shown no response to such treatment for at least about 4 weeks, or at least about 8 weeks, or at least about 12 weeks of treatment.

The cancer can be any cancer treatable by immune checkpoint inhibitor therapy, including primary cancer or a metastatic cancer or hematological cancer, and may have an origin from any tissue. For example, in embodiments, the cancer originates from skin, colon, breast, or prostate, and thus is made up of cells that were originally skin, colon, breast, or prostate, respectively.

In some embodiments, the cancer is progressive, locally advanced, or metastatic carcinoma. In some embodiments, the cancer is metastatic melanoma, and may be recurrent. In some embodiments, the metastatic melanoma is stage III or IV, and may be stage IVA, IVB, or IVC. The metastasis may be regional or distant.

In some embodiments, the solid tumor is a sarcoma or carcinoma. In some embodiments, the solid tumor is a relapsed or refractory solid tumor. In some embodiments, the relapsed or refractory solid tumor is a sarcoma or carcinoma. In some embodiments, the solid tumor is a metastasized solid tumor. In some embodiments, the metastasized solid tumor is a sarcoma or carcinoma.

In some embodiments, the cancer is a hematological cancer. In some embodiments, the hematologic cancer is a leukemia (e.g., AML), a lymphoma, a myeloma, a non-Hodgkin's lymphoma, a Hodgkin's lymphoma, a T-cell malignancy, or a B-cell malignancy.

Other aspects and embodiments of the invention will be apparent from the following examples.

EXAMPLES

Example 1: In Vivo Model for Leaky Gut Associated with NASH Liver Pathology

Decline in gut integrity ("leaky gut") can occur in the progression of NAFLD and NASH. A modified competition ELISA enabling serial serum dextran measurements in small volumes of serum was used to measure gut integrity, and demonstrates that administration of larazotide acetate improves gut integrity in this in vivo model.

Figure 1:
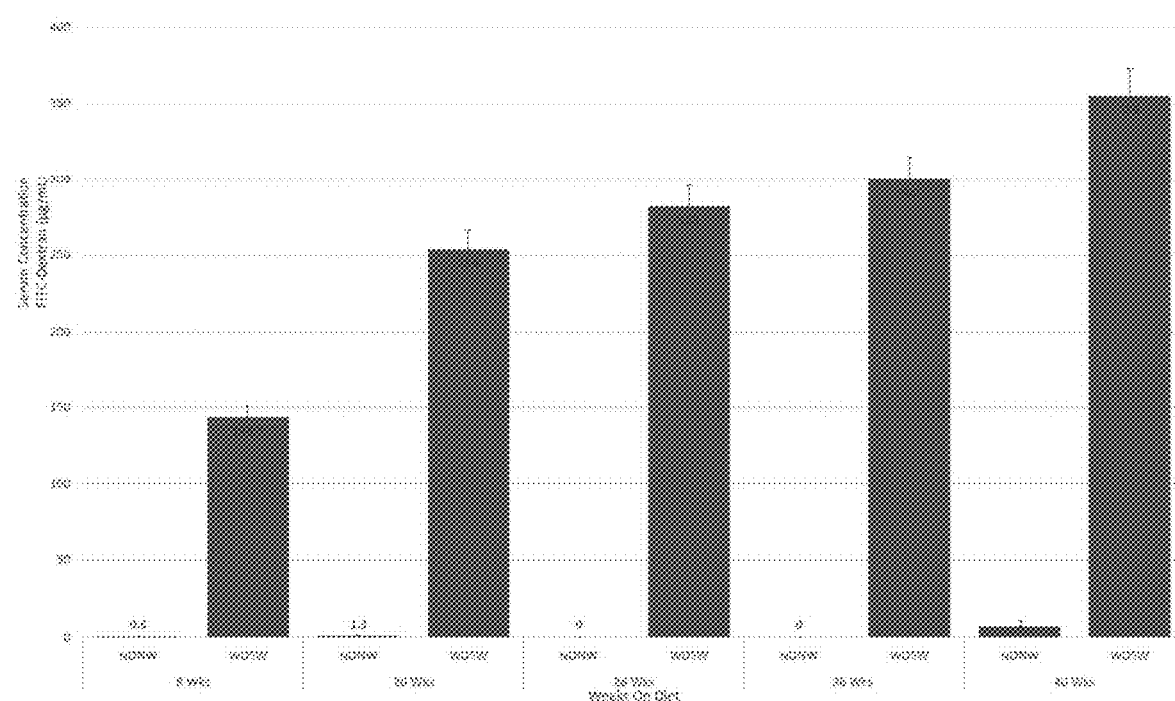
FIG. 1 shows that mice within a Western diet group had significantly higher serum dextran levels, a measure of gut integrity, as compared to the normal diet group.

77 DIAMOND™ mice were placed on either normal chow (NDNW) or Western Diet (WDSW) and aged up to 8, 20, 28, 36, and 40 weeks, then dosed with 4 kDa FITC-dextran at 600 mg/kg body weight by gavage. Four hours after the dosing, at least 20 µL of serum was taken by tail vein nick. A competition ELISA, which measures small dextran polymers (conjugated or unconjugated), was used to quantify serum dextran concentration. It was observed that serum dextran levels were significantly higher in the Western diet group as compared to the normal diet group, as shown in FIG. 1.

The subsequent experiment evaluated the effects of orally administered larazotide acetate to mice on the Western diet. The study design is depicted in FIG. 2. Specifically, 8 groups of mice were placed on WDSW diets for 16 weeks and administered larazotide (dosed in drinking water or oral gavage), pioglitazone comparator, or vehicle from 8-16 weeks. Improvement in leaky gut was assessed by dosing the mice with unconjugated dextran at 600 mg/kg via oral gavage at baseline and end of study, serum was collected 4 hours later, and serum dextran concentrations were measured.

Figure 3:
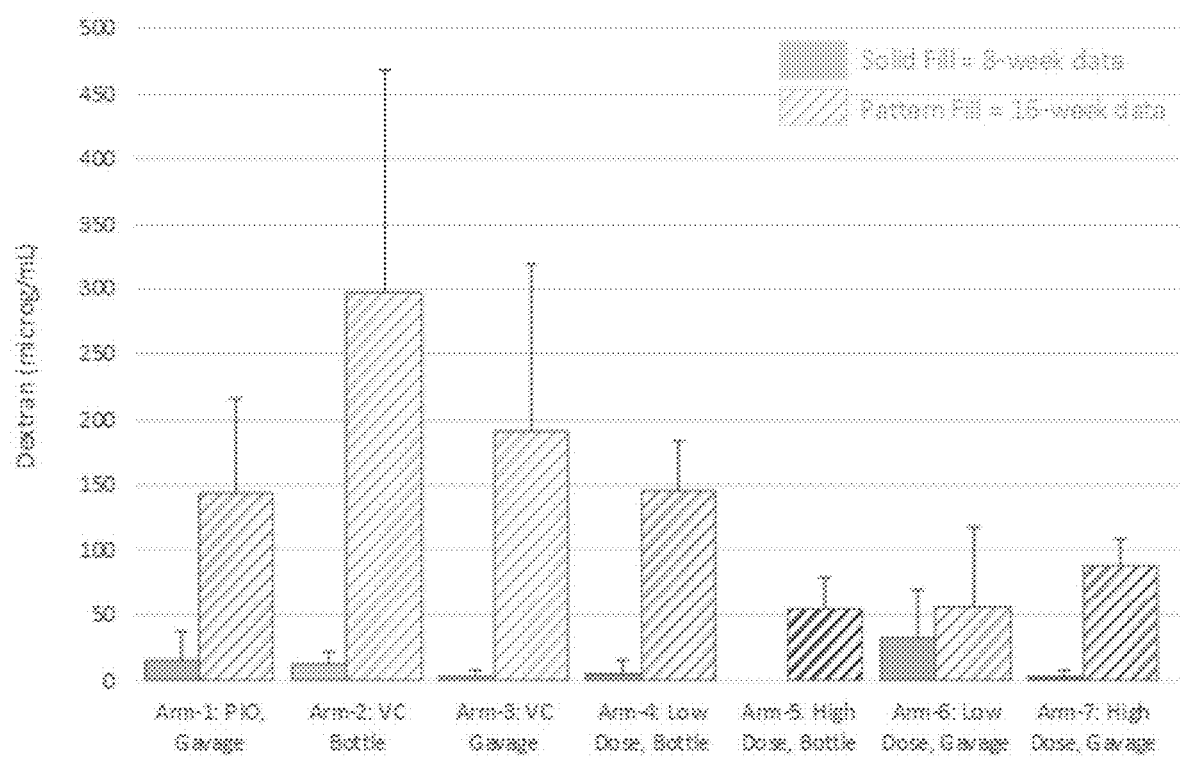
FIG. 3 shows that orally administered larazotide to mice subsisting on the Western diet showed improved gut integrity.
Figure 4:
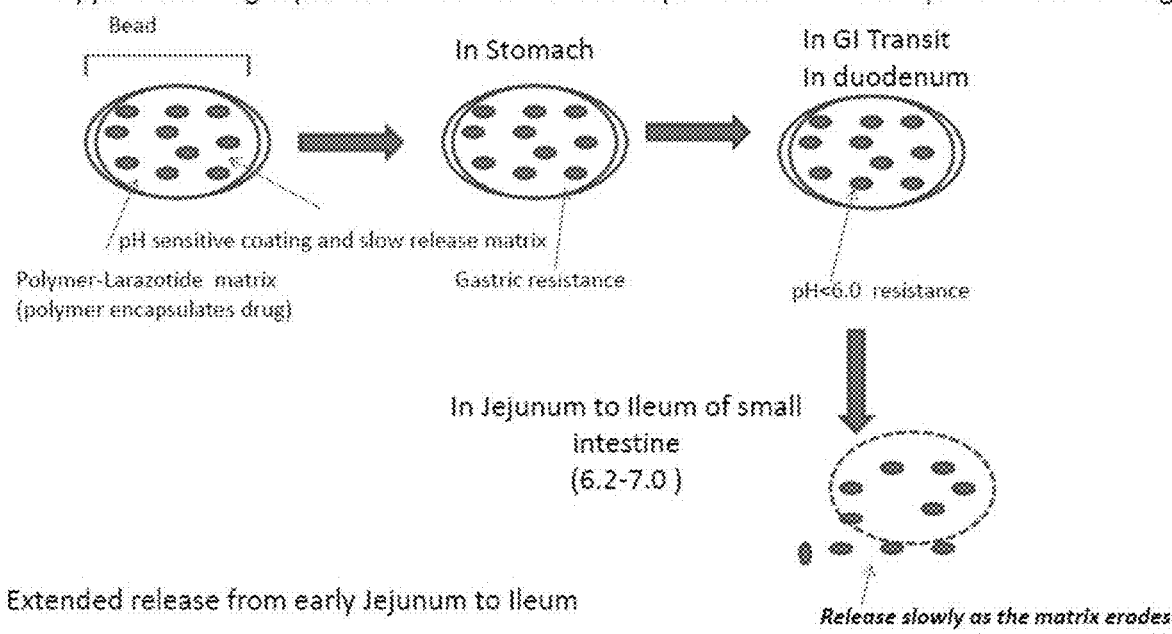
FIG. 4 illustrates an exemplary formulation of larazotide for sustained delivery to the early jejunum and ileum.

FIG. 3 shows that larazotide administration improved gut integrity in the mouse model, as measured by serum dextran concentration. FIG. 3 shows that various doses of larazotide acetate were successful in lowering the serum dextran concentrations in mice on Western diets.

Example 2: Multiple Dosing of Larazotide is Effective at Low Concentrations

The purpose of this experiment was to determine the therapeutic effect of fractional dosing of larazotide at small concentrations. Indeed, this experiment verifies the inverse dose response shown by larazotide due to the local buildup of inactive larazotide fragments that results from administration of excessive amounts of larazotide. Therefore, this experiment supports the theory that low doses of larazotide work best by avoiding the reservoir of competing inactive fragments.

In an ex-vivo ischemic jejunum model measuring TER (transepithelial resistance), various concentrations (0.1 µM, 0.5 or 1 µM) of larazotide were administered every 45 minutes in fractional doses. As denoted by the arrows along the x-axis of FIG. 10, the fractional doses were administered at 45 minutes, 90 minutes, 135 minutes, and 180 minutes. FIG. 10 shows that multiple dosing of larazotide at low concentrations (e.g., 0.1 µM) is more effective, as compared to a single dose of larazotide at 1 µM over the recovery period of at least 240 minutes.

In particular, Yorkshire-cross pigs of 6-8 weeks of age were anesthetized, followed by midline laparotomy and creation of a series of 10 cm intestinal loops (jejunum) commencing proximal to the ileum by ligating the intestinal lumen. Mesenteric vasculature was ligated to select treatment loops for 45 minutes, whereas other loops were left as non-ischemic controls. Loops were subsequently resected, and the mucosal tissues were stripped in oxygenated (95% $O_2$/5% $CO_2$) Ringers solution from the muscle layers in preparation for ex vivo incubation. Tissues were then mounted on Ussing chamber, and all tissues were allowed to acclimate for a period of 30 minutes to establish baseline measurements. The tissues were treated with various concentrations of larazotide at various time intervals and were monitored by measuring transepithelial electrical resistance (TEER) for up to 240 minutes.

Accordingly, the results of this experiment support the conclusion that releasing small amounts of larazotide over an extended period of time improves the effect of the active agent.

Example 3: Sustained Release Tablet Formulation

The following example illustrates preparation of an enteric-coated tablet for sustained release of larazotide to the jejunum and ileum.

TABLE 1

Composition of core tablet (% wt)

| Component | F23 |
|---|---|
| Larazotide | 1 |
| Sodium carboxymethylcellulose | 48.5 |
| Magnesium Stearate | 0.5 |
| HPMC | 50 |

TABLE 2

Compounding table of core tablet (mg/3000 mg)

| Component | F23 |
|---|---|
| Larazotide | 30 |
| Sodium carboxymethylcellulose | 1455 |
| Magnesium Stearate | 15 |
| HPMC | 1500 |

TABLE 3

Composition of enteric coating solution (% wt)

| Component | F23 |
|---|---|
| Eudragit L100 | 6 |
| Triethyl Citrate | 0.6 |
| Ethanol | 93.4 |

TABLE 4

Compounding table of enteric coating solution (g/250 g)

| Component | F23 |
|---|---|
| Eudragit L100 | 15 |
| Triethyl Citrate | 1.5 |
| Ethanol | 233.5 |

The following process was used for preparing the core tablet. API, HPMC, Sodium carboxymethylcellulose, and Magnesium Stearate were weighed out in a mortar and mixed well. 100 mg of the mixture was weighed out to make a core tablet. The core tablets were divided into 3 portions: (1) tablets without further coating, coded as F23-1; (2) tablets with enteric coating, coded as F23-2; and (3) press coated with one layer of HPMC, followed by another enteric coating layer, samples are coded as F23-3.

The enteric-coating was made by the following process. Eudragit L100 and Triethyl Citrate was weighed out in a glass bottle according to the enteric-coating compounding table.

Ethanol was added to dissolve the powders. The tablets were dipped in the enteric coating solution, followed by N2 blow drying, which was repeated until the weight gain is about 10%.

TABLE 5

Dissolution results

| Medium | Time point (min) | % Release |
|---|---|---|
| F23-1 (Core tablet without enteric coating) | | |
| SGF pH 1.1 | 30 | 13.3 |
| | 120 | 35.6 |
| SIF pH 5.5 | 15 | 35.6 |
| | 30 | 41.4 |
| | 60 | 42.2 |
| | 90 | 46.1 |
| | 120 | 61.5 |
| SIF pH 7.0 | 15 | 61.5 |
| | 30 | 61.5 |
| | 60 | 66.3 |
| | 90 | 74.8 |
| | 120 | 69.8 |
| | 180 | 73.0 |
| | 240 | 76.9 |
| | 300 | 91.3 |
| | 360 | 89.5 |
| F23-2 (Core tablet with enteric coating) | | |
| SGF pH 1.1 | 30 | 0.0 |
| | 120 | 0.0 |
| SIF pH 5.5 | 15 | 0.0 |
| | 30 | 0.0 |
| | 60 | 0.0 |
| | 90 | 2.1 |
| | 120 | 5.4 |

TABLE 5-continued

Dissolution results

| Medium | Time point (min) | % Release |
|---|---|---|
| SIF pH 7.0 | 15 | 5.4 |
| | 30 | 12.8 |
| | 60 | 14.4 |
| | 90 | 19.4 |
| | 120 | 31.0 |
| | 180 | 38.4 |
| | 240 | 46.3 |
| | 300 | 61.4 |
| | 360 | 61.5 |

Conclusions:

HPMC and Sodium CMC can extend the release time of larazotide.

L100 enteric coating can prevent larazotide from releasing in SGF dissolution medium.

Figure 5:
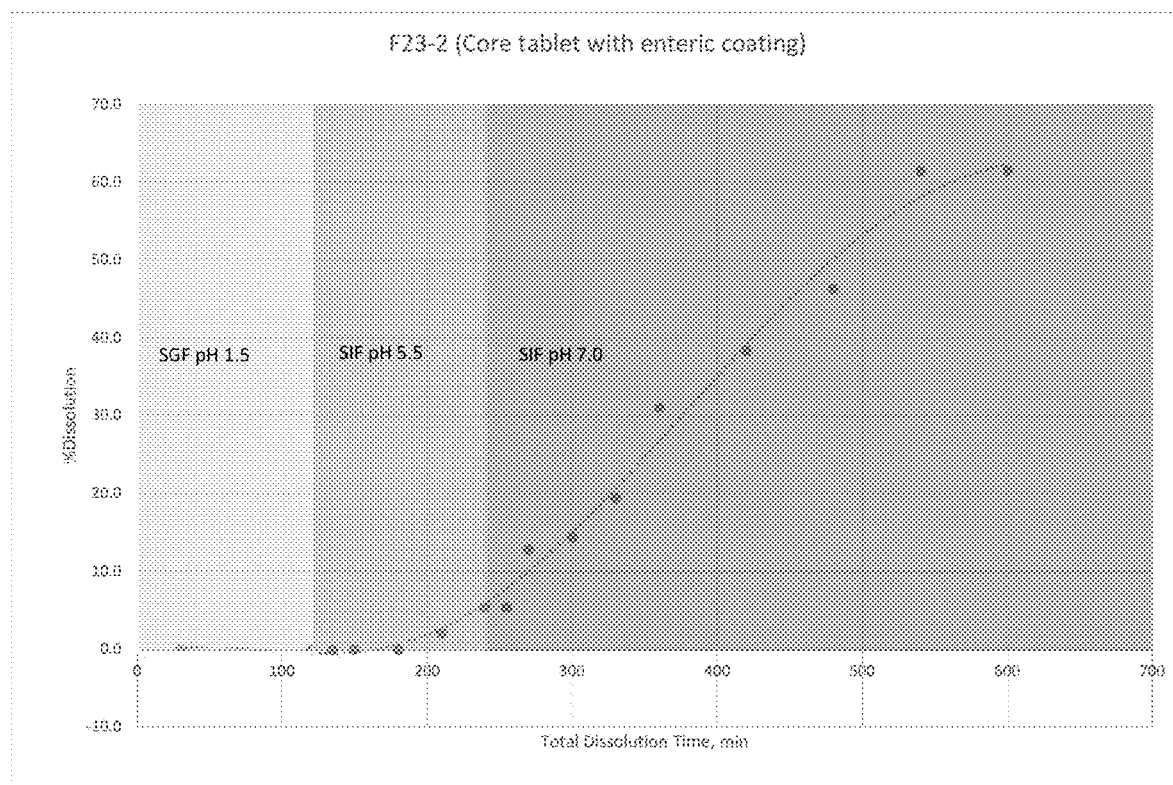
FIG. 5 shows the results of a dissolution test of an enteric-coated tablet (F23-2 in Example 3).

F23-2 met the requirement of no more than 5% of total API released at 2 hours in SGF and no more than 20% of total API released at 2 hours in SIF (pH 5.5). See FIG. 5.

Example 4: Core Granules and Enteric Coating Allow for Controlled Release Formulation The objective of this experiment was to compare release profiles and dissolution results for two controlled release larazotide particulate formulations comprising different composition make-ups and enteric coatings.

Core granules were produced through a wet granulation process. Core granule A was composed of the following: larazotide, hydroxypropyl methylcellulose (HPMC), Pharmacel® 101 microcrystalline cellulose (MCC), and magnesium stearate. Core granule B was composed of the following: larazotide, Kollidon® VA64, Pharmacel® 101 microcrystalline cellulose (MCC), and magnesium stearate. The composition formulas are produced in Table 1 below.

TABLE 6

Composition of core granule (% wt)

| Component | A | B |
|---|---|---|
| Larazotide | 1 | 1 |
| HPMC | 3 | |
| Kollidon VA64 | | 5 |
| MCC | 95.5 | 93.5 |
| Magnesium Stearate | 0.5 | 0.5 |

The wet granulation process began by mixing and weighing each of the components and then gradually adding DI water to the mixture in order to form a dough. The dough was then extruded through a 1.0 mm dome sieve at 45 r.p.m. by an extruder (Multi-Gran, Fuji Paudal, Model: MG-55). Extrudates were collected and poured into a Marumerizer (Benchtop marumerizer, Fuji Paudal, Model: QJ-230T-1) and run at 1,800 r.p.m./1,300 r.p.m. for 2 minutes/1 minute to create the granules. Granules were dried for 3 hours and then tested for water content using a moisture analyzer (Mettler Toledo, Model: HR73). After, the dried granules were put through sieve no. 18 (Fisher Scientific, 1.00 mm) and sieve no. 25 (Fisher Scientific, 710 μm).

Two enteric coating solutions were prepared in order to compare their release profiles when coated onto core granule A and core granule B. S100 enteric coating solution was prepared by weighing out Eudragit® and triethyl citrate and then adding ethanol and talc. The composition of both enteric coatings is depicted in Table 2.

TABLE 7

Composition of enteric coating (% wt)

| Component | FS30D | S100 |
|---|---|---|
| Eudragit FS30D | 60.61 | |
| Eudragit S100 | | 6 |
| Triethyl Citrate | | 0.6 |
| Talc | | 3 |
| Ethanol | | 90.4 |
| Water | 30.3 | |
| PlasACRYL | 9.09 | |

The granules were then dipped in the S100 enteric coating solution, followed by N2 blow-drying. This step was repeated until specific weight gained was achieved, as depicted in Table 3.

TABLE 8

S100 weight gained for each of core granules A and B

| Name | Enteric Solution | % Weight Gained |
|---|---|---|
| A | S100 | 50 |
| B-1 | S100 | 30 |
| B-2 | S100 | 90 |

FS30D enteric coating solution was prepared by shaking PlasACRYL and adding Eudragit® FS30D and water into the PlasACRYL while stirring. The composition of the FS30D enteric coating is depicted in Table 2. The granules were then sprayed with the FS30D enteric coating while stirring, followed by N2 blow-drying. This step was repeated until specific weight gained was achieved, as depicted in Table 9.

TABLE 9

FS30D weight gained for each of core granules A and B

| Name | Enteric Solution | % Weight Gained |
|---|---|---|
| B-3 | FS30D | 10 |
| B-4 | FS30D | 23 |
| B-5 | FS30D | 50 |
| B-6 | FS30D | 90 |

In vitro dissolution testing was then performed on each of the coated core granules under the conditions depicted in Table 10.

TABLE 10

In vitro dissolution method settings

| System | HP Agilent 1100 |
|---|---|
| Apparatus | USP Apparatus 1 (Basket) |
| Temperature | 37.0 ± 0.5° C. |
| Rotation Speed | 100 rpm |

| | Acid Stage | SGF |
|---|---|---|
| Medium | pH 5.5, Buffer stage | SIF, pH 5.5 ± 0.05 |
| | pH 7.0, Buffer stage | SIF, pH 7.0 ± 0.05 |

TABLE 10-continued

In vitro dissolution method settings

| | | |
|---|---|---|
| Medium Volume | | 200 mL |
| Sampling Time Point | SGF pH 1.1 | 30, 60 and 120 minutes |
| | SIF pH 5.5 | 15, 30, 60, 90 and 120 minutes |
| | SIF pH 7.0 | 15, 30, 60, 90, 120, 180, 240, 300 and 360 minutes |
| Sampling Volume | | 1 mL |
| Sample Filter | | 10 μm |

The process began by weighing out the granules into a capsule and then loading the capsule or table into a basket. A specific volume of pH 1.0 SGF dissolution medium was then added into a vessel and heated up to 37.0±0.5° C. The basket containing the granules was then placed inside the vessel. An auto-sampler was set to procure about 1 mL samples at the time points listed in Table 5. After 120 minutes, the dissolution was stopped by raising the baskets and the media was discarded. Once a specific volume of pre-warmed pH 5.5 SIF dissolution medium was transferred into the vessel (with stirring), the baskets were lowered again. At the stated sampling times in Table 5, 1 mL solution samples were taken by the auto-sampler. After 120 minutes, the dissolution was stopped again by raising the baskets and the media was discarded. A specific volume of pre-warmed pH 7.0 SIF dissolution medium was transferred into the vessel (with stirring) and the baskets were lowered once more. At the stated sampling times in Table 10, 1 mL solution samples were taken by the auto-sampler.

The results of the dissolution tests for various core granules and enteric coatings/enteric coating thickness are depicted in Table 11 and FIGS. 6A-F.

TABLE 11

Dissolution results for core granules A and B

| Medium | Time point (min) | % Release |
|---|---|---|
| Core granule A with S100 enteric coating, 50% weight gained | | |
| SGF pH 1.0 | 30 | 4.3 |
| | 60 | 13.3 |
| | 120 | 25.0 |
| SIF pH 5.5 | 30 | 30.1 |
| | 60 | 34.4 |
| | 90 | 38.3 |
| | 120 | 40.0 |
| SIF pH 7.0 | 30 | 45.2 |
| | 60 | 50.7 |
| | 90 | 53.9 |
| | 120 | 57.0 |
| | 180 | 64.8 |
| | 240 | 70.0 |
| Core granule B-1 with S100 enteric coating, 30% weight gained | | |
| SGF pH 1.0 | 30 | 5.9 |
| | 60 | 16.6 |
| | 120 | 33.3 |
| SIF pH 5.5 | 30 | 41.6 |
| | 60 | 46.6 |
| | 90 | 51.0 |
| | 120 | 55.8 |
| SIF pH 7.0 | 30 | 63.3 |
| | 60 | 68.3 |
| | 90 | 73.0 |
| | 120 | 78.3 |
| | 180 | 83.9 |
| | 240 | 87.7 |

TABLE 11-continued

Dissolution results for core granules A and B

| Medium | Time point (min) | % Release |
|---|---|---|
| Core granule B-2 with S100 enteric coating, 90% weight gained | | |
| SGF pH 1.0 | 30 | 2.0 |
| | 60 | 4.7 |
| | 120 | 9.6 |
| SIF pH 5.5 | 30 | 12.1 |
| | 60 | 14.2 |
| | 90 | 15.9 |
| | 120 | 19.0 |
| SIF pH 7.0 | 30 | 24.4 |
| | 60 | 27.9 |
| | 90 | 33.6 |
| | 120 | 38.8 |
| | 180 | 45.8 |
| | 240 | 51.7 |
| Core granule B-3 with FS30D enteric coating, 10% weight gained | | |
| SGF pH 1.0 | 30 | 41.4 |
| | 60 | 69.2 |
| | 120 | 88.3 |
| SIF pH 5.5 | 30 | 91.0 |
| | 60 | 91.7 |
| | 90 | 92.3 |
| | 120 | 92.3 |
| SIF pH 7.0 | 30 | 92.3 |
| | 60 | 93.5 |
| | 90 | 94.5 |
| | 120 | 94.6 |
| | 180 | 94.2 |
| | 240 | 95.0 |
| Core granule B-4 with FS30D enteric coating, 23% weight gained | | |
| SGF pH 1.0 | 30 | 1.4 |
| | 60 | 3.1 |
| | 120 | 5.6 |
| SIF pH 5.5 | 30 | 7.3 |
| | 60 | 8.1 |
| | 90 | 10.0 |
| | 120 | 11.8 |
| SIF pH 7.0 | 30 | 15.6 |
| | 60 | 30.2 |
| | 90 | 53.5 |
| | 120 | 71.8 |
| | 180 | 88.6 |
| | 240 | 100.0 |
| Core granule B-5 with FS30D enteric coating, 50% weight gained | | |
| SGF pH 1.0 | 30 | 0.0 |
| | 60 | 0.0 |
| | 120 | 2.9 |
| SIF pH 5.5 | 30 | 2.9 |
| | 60 | 2.9 |
| | 90 | 2.9 |
| | 120 | 2.9 |
| SIF pH 7.0 | 30 | 2.9 |
| | 60 | 2.9 |
| | 90 | 2.9 |
| | 120 | 7.4 |
| | 180 | 15.8 |
| | 240 | 33.8 |
| Core granule B-6 with FS30D enteric coating, 90% weight gained | | |
| SGF pH 1.0 | 30 | 0.0 |
| | 60 | 0.0 |
| | 120 | 0.0 |
| SIF pH 5.5 | 30 | 0.0 |
| | 60 | 0.0 |
| | 90 | 0.0 |
| | 120 | 0.0 |
| SIF pH 7.0 | 30 | 0.0 |
| | 60 | 0.0 |
| | 90 | 0.0 |
| | 120 | 0.0 |
| | 180 | 0.0 |
| | 240 | 0.0 |

A summary of the formulation and their various properties, including dissolution profiles, is depicted in Table 12.

TABLE 12

Summary of formulation properties

| Name | Binder | Enteric coating | % Weight gained after coating | % Dissolution at 2 hr in SGF | % Dissolution at 2 hr in SIF, pH 5.5 | % Dissolution at 4 hr in SIF, pH 7.0 |
|---|---|---|---|---|---|---|
| A | HPMC | S100 | 50 | 25.0 | 40.0 | 70.0 |
| B-1 | Kollidon | S100 | 30 | 33.3 | 55.8 | 87.7 |
| B-2 | Kollidon | S100 | 90 | 9.6 | 19.0 | 51.7 |
| B-3 | Kollidon | FS30D | 10 | 88.3 | 92.3 | 95.0 |
| B-4 | Kollidon | FS30D | 23 | 5.6 | 11.8 | 100.0 |
| B-5 | Kollidon | FS30D | 50 | 2.9 | 2.9 | 33.8 |
| B-6 | Kollidon | FS30D | 90 | 0.0 | 0.0 | 0.0 |

When compared against the S100 enteric coating, the FS30D enteric coating was shown to produce more favorable release properties of the API (i.e., larazotide). In addition, it was found that increasing the enteric coating weight gained could decrease the release of the API; however, too much coating resulted in slow API release at higher pH. A balance was struck with B-4 (23% weight gained), such that the formulation retained slow release at low pH (<5.5) and fast release at high pH (>7).

Example 5: In Vivo Release Profile of Controlled Release Larazotide Particulate Formulations The purpose of this experiment was to establish the in vivo release profile of larazotide in the delayed and extended release formulation of B-4.

Figure 7:
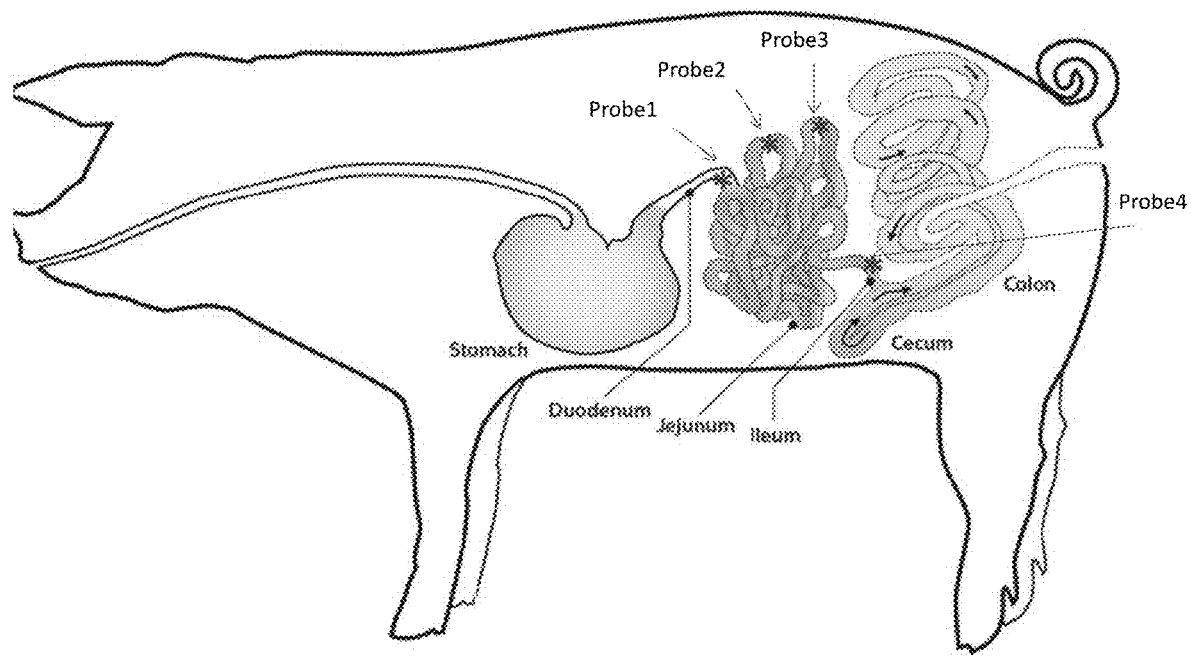
FIG. 7 depicts an animal model of an experiment for showing the in vivo release profile of larazotide in the delayed and time slow release formulation B-4 in the pig GI tract. Probe 1 was directed to the duodenum (8-10 cm from the pylorus); Probe 2 was directed about 20 cm from Probe 1; Probe 3 was directed about 50 cm from Probe 1; and Probe 4 was directed to the cecum-ileum junction.

Because the human digestive system and pig's digestive system are similar, the pig GI tract was used as a model for this experiment, as depicted in FIG. 7. Probe 1 was directed to the duodenum (8-10 cm from the pylorus); Probe 2 was directed about 20 cm from Probe 1; Probe 3 was directed about 50 cm from Probe 1; and Probe 4 was directed to the cecum-ileum junction.

In particular, male pigs of 6-8 weeks of age with weights between 12-18 kg were used at the beginning of the study. The ultrafiltration (UF) probes were placed in the intestine surgically. Food and water were withheld from pigs at least 12 hours prior to anesthesia and surgery. Surgical midline abdominal incision laparotomy was used to implant ultrafiltration probes on the inside walls of the intestine. Ultrafiltration probe tubing tunneled through the skin and attached to skin with sutures. A collection tube was attached to the outer end of each probe tubing for sampling gastrointestinal fluid. The first probe was placed at 8-10 cm from the pylorus (end of duodenum), and the second probe was placed 20 cm distal to the first probe (within jejunum). The third probe was placed 50 cm distal to the first probe (within jejunum), and the fourth probe was placed at the cecum-ileum junction. Animals were fasted at least 12 hours prior to each dose and 4 hours following each dosing event. Water was withheld 1 hour prior to dosing and 2 hours after dosing. Dosing was chased with 120 ml water. Gastrointestinal fluid was sampled from the filtered samples obtained from the collection tube for each probe prior to dosing, and 0-1 hour, 1-2 hours, 2-3 hours, 3-4 hours, 4-5 hours after dosing. Larazotide concentrations from gastrointestinal fluid samples were determined using a UPLC-MS/MS method.

Figure 8:
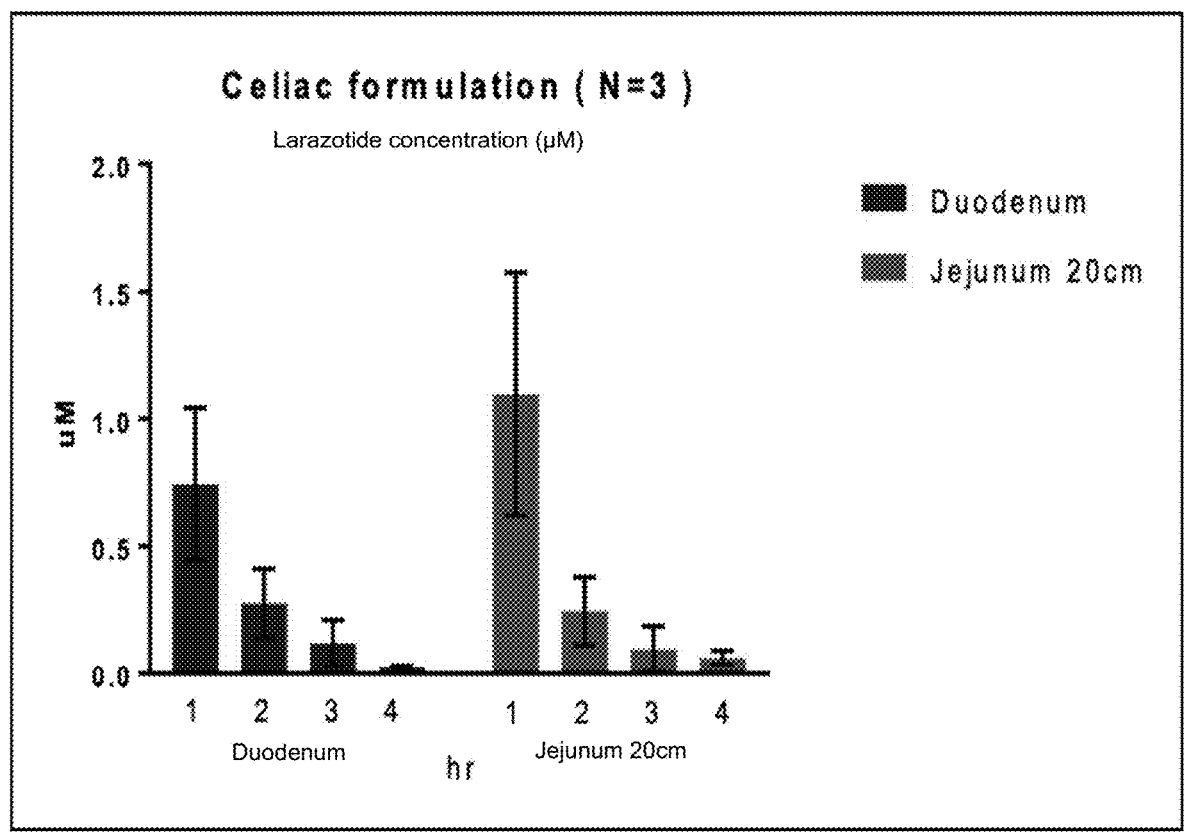
FIG. 8 depicts the in vivo release profile of the delayed release larazotide formulation containing two bead populations delivering larazotide acetate to the duodenum and jejunum, which is used in the treatment of celiac disease.
Figure 9:
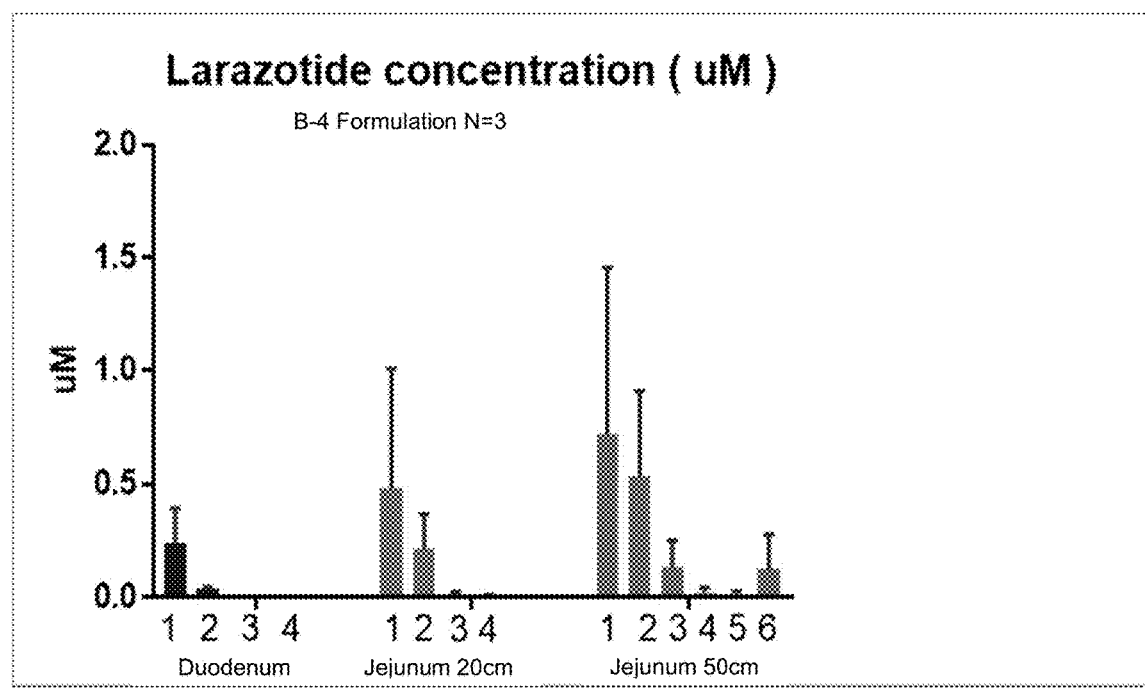
FIG. 9 shows the in vivo release profile of the delayed and extended release B-4 formulation.

For the sake of comparison, FIG. 8 depicts in vivo release profile of the delayed release larazotide formulation, while FIG. 9 shows the in vivo release profile of the delayed and extended release B-4 formulation. The delayed release larazotide formulation used in FIG. 8 was formulated for the treatment of celiac disease, and it has two beads, both of which are gastroresistant (that is, they do not release in simulated gastric fluid (SGF)). The first bead releases within 60 minutes in simulated intestinal fluid (SIF) having a pH of greater than 5, once the bead reaches the duodenum, and the second bead releases by about 30 minutes and about 90 minutes later (in SIF), targeting the jejunum.

Figure 6A:
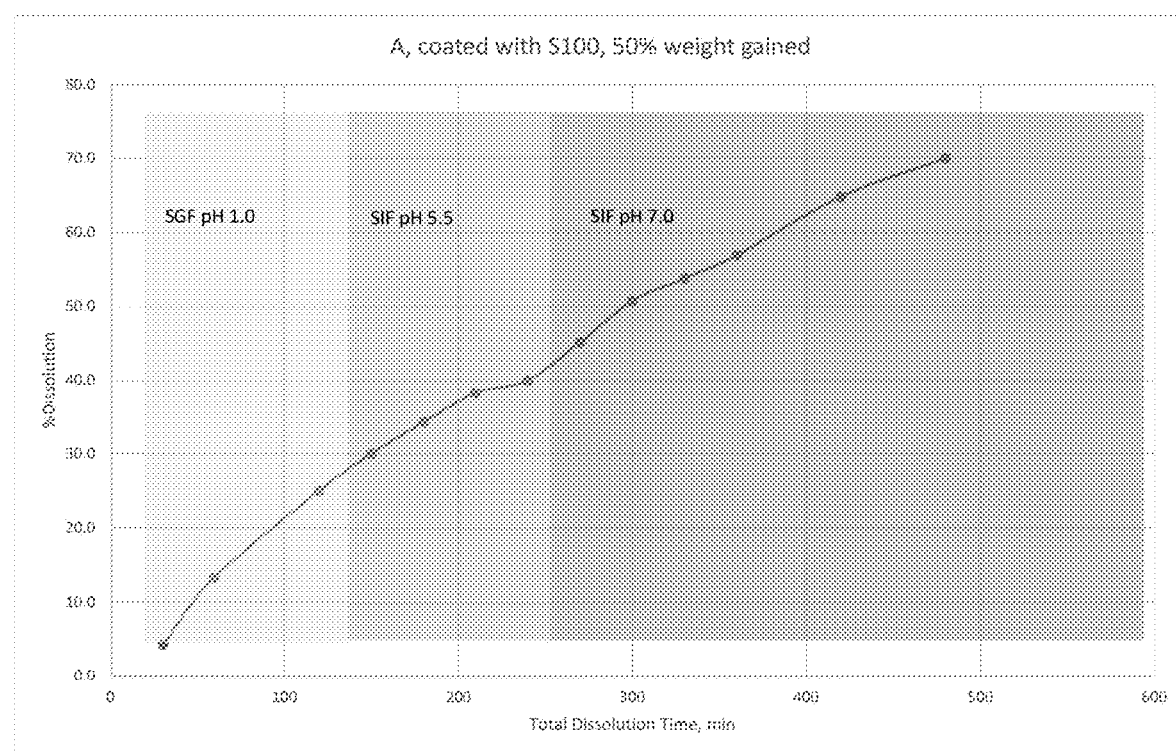
FIG. 6A-F depicts the results of in vitro dissolution tests for various formulations: core granule A with S100 enteric coating, 50% weight gained (FIG. 6A); core granule B-1 with S100 enteric coating, 30% weight gained (FIG. 6B); core granule B-2 with S100 enteric coating, 90% weight gained (FIG. 6C); core granule B-3 with F30D enteric coating, 10% weight gained (FIG. 6D); core granule B-4 with F30D enteric coating, 23% weight gained (FIG. 6E); and core granule B-5 with F30D enteric coating, 50% weight gained (FIG. 6F).
Figure 6B:
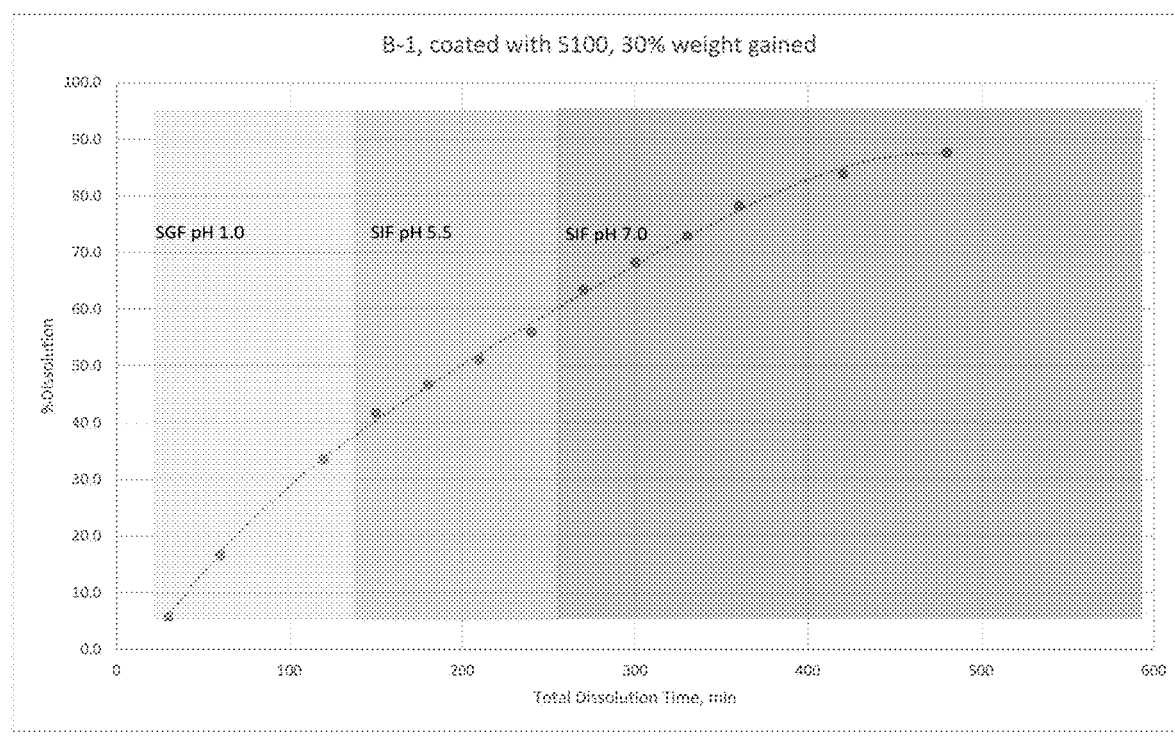
Figure 6C:
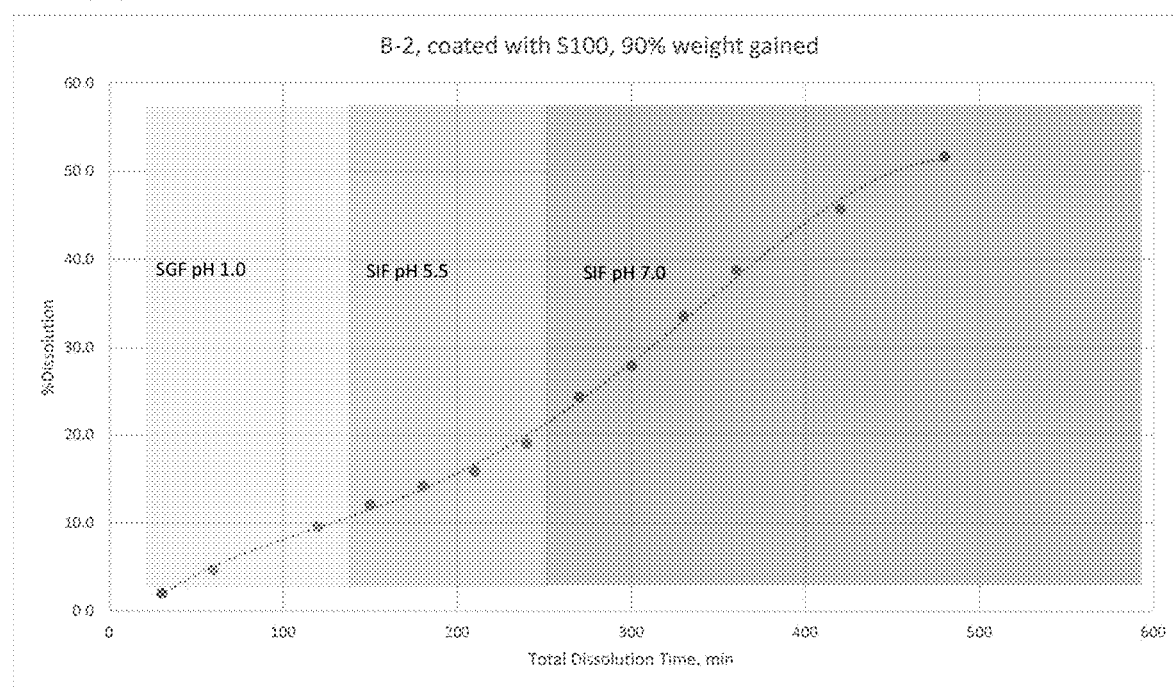
Figure 6D:
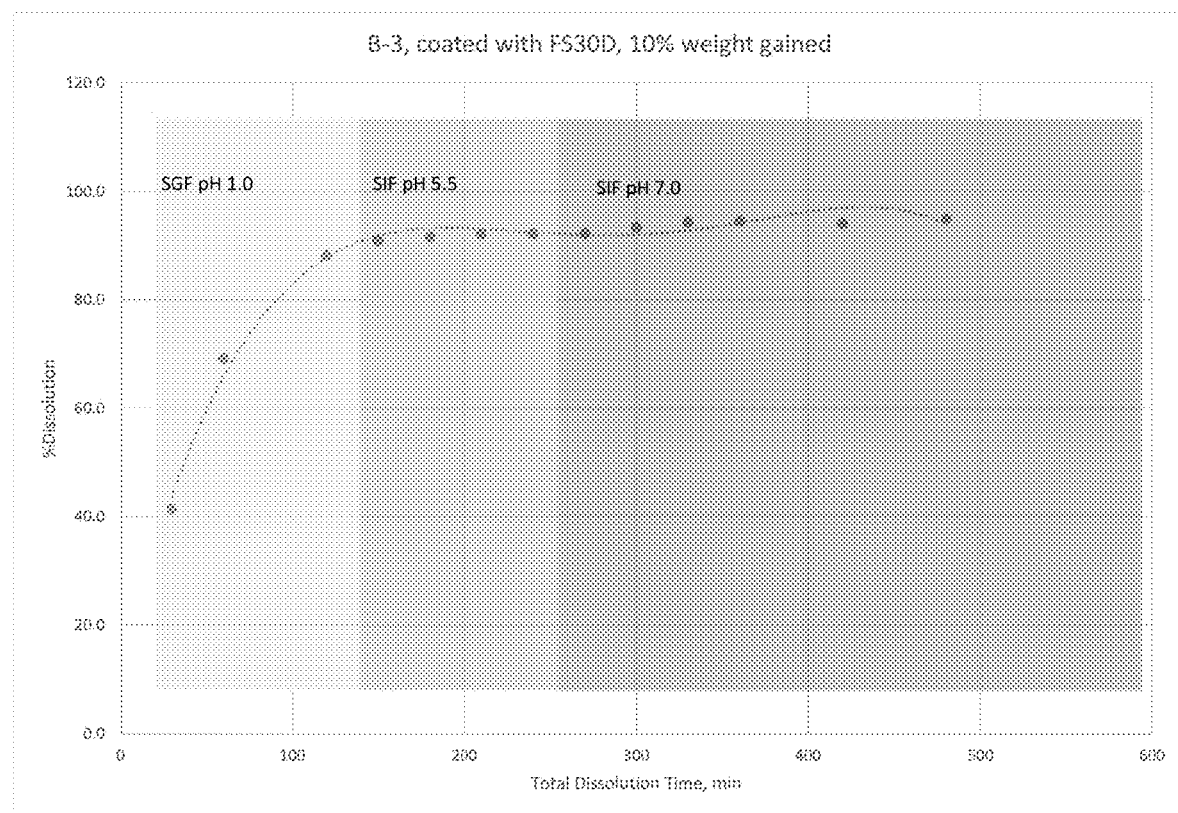
Figure 6E:
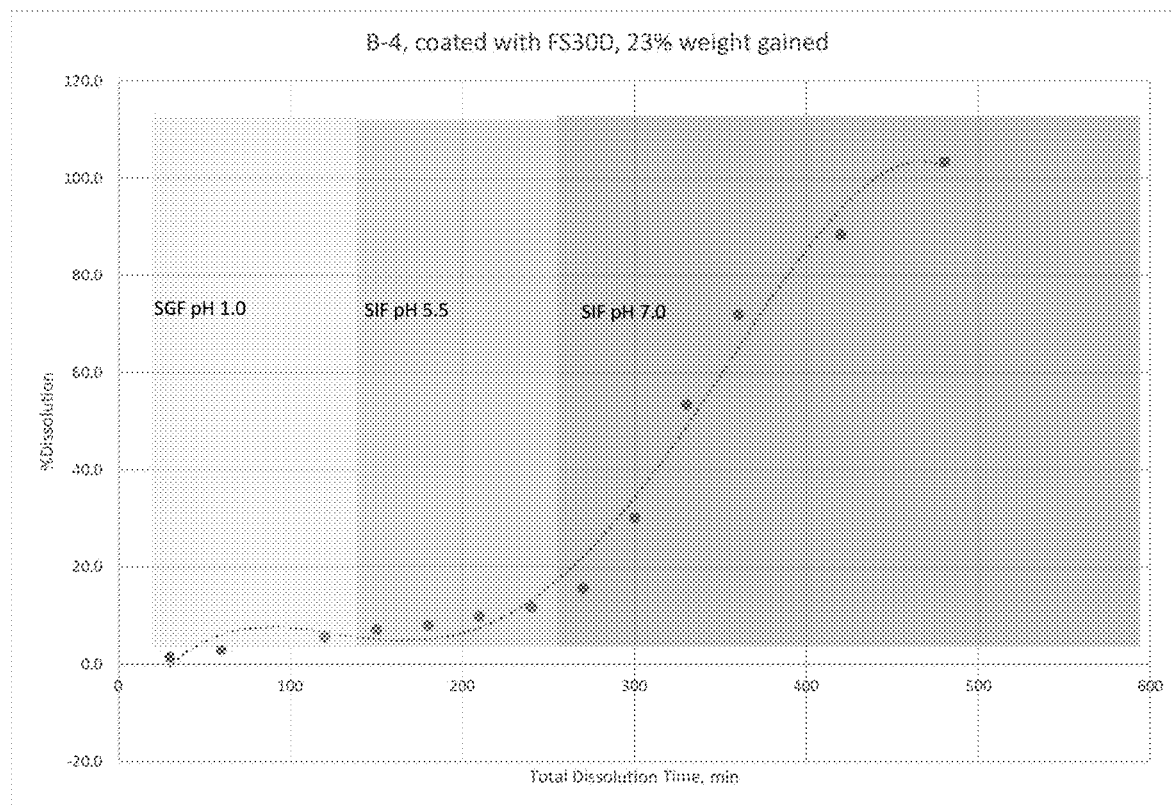
Figure 6F:
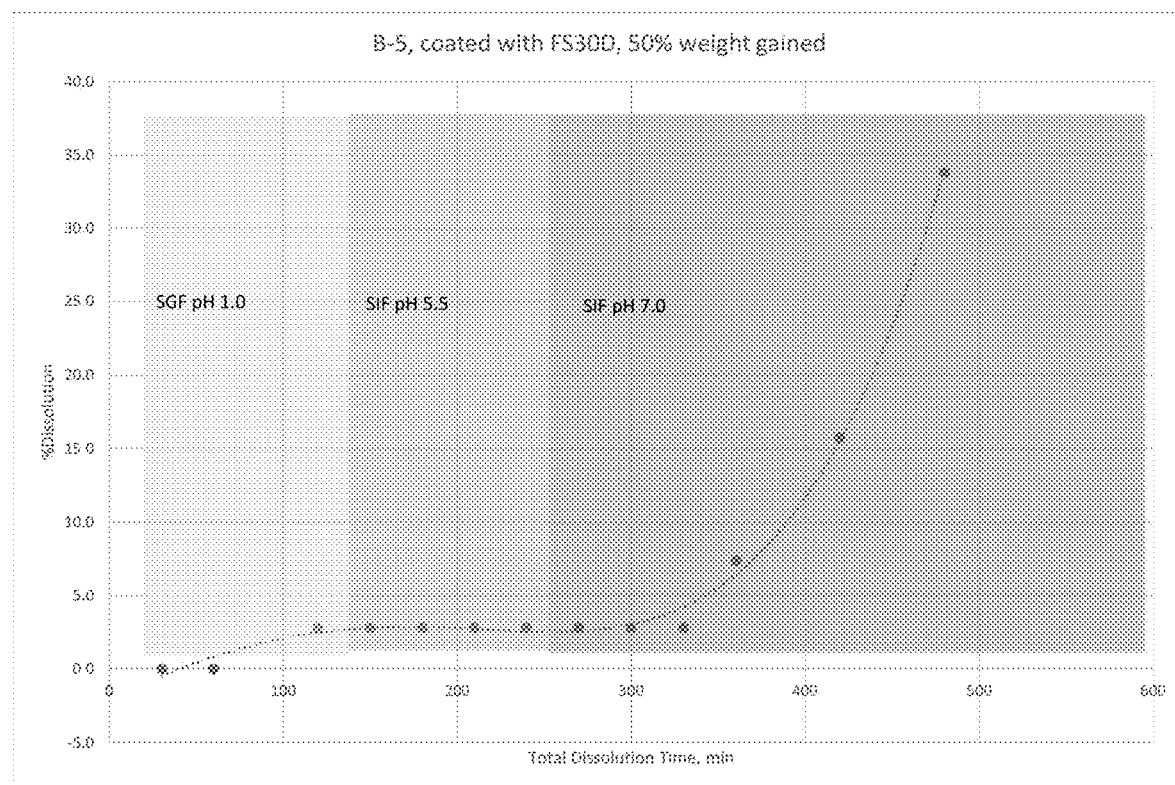

Whereas a 1 mg dose of the delayed release formulation of FIG. 8 only releases in the duodenum and jejunum (20 cm), the delayed and extended release B-4 formulation of FIG. 9 releases only a small amount in the duodenum, and larger amounts in the jejunum (20 cm) and jejunum (50 cm). This result is supported by the in vitro release profile of B-4, as depicted in FIG. 6E, where the formulation delayed release until it had reached the jejunum and from there it exhibited a slow release (over 180 minutes) from the jejunum to the ileum.

Example 6: Storage Stability Study of 10 g Batch of Extended Release B-4 Formulation (Appearance, Assay and Impurity)

B-4 larazotide granules (lot #339-2-83) were tested for appearance, assay and impurity at T0 and T=3 months with the analytical method for Larazotide, with the results shown in Tables 13 and 14 below.

TABLE 13

Results for B-4 larazotide granule appearance and assay.

| Conditions | Appearance | API/Drug, mg/g (Assay) | % Recovery vs. T = 0 |
|---|---|---|---|
| T = 0 | Off-white granules | 7.7 | N/A |
| 2-8° C., 3 months | Off-white granules | 7.9 | 102.2 |
| 25° C., 3 months | Off-white granules | 7.4 | 96.6 |

TABLE 14

Results for B-4 larazotide granule impurity.

| Conditions | % Purity | % IMP, RRT = 1.07 | % IMP, RRT = 1.17 | % IMP, RRT = 1.36 | % IMP, RRT = 1.59 | % IMP, RRT = 1.68 | % IMP, RRT = 2.00 |
|---|---|---|---|---|---|---|---|
| T = 0 | 97.3 | 0.82 | 0.57 | 0.79 | 0.42 | N/A | 0.12 |
| 2-8° C., 3 months | 97.8 | 0.63 | 0.34 | 0.90 | 0.16 | N/A | 0.20 |
| 25° C., 3 months | 98.0 | 0.40 | 0.35 | 0.68 | 0.22 | 0.23 | 0.13 |

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. An oral composition comprising an effective amount of a peptide that is larazotide or a larazotide derivative, or salt thereof, contained within a biodegradable or erodible polymer matrix comprising microcrystalline cellulose that provides for sustained release of the peptide in simulated intestinal fluid having a pH of 7.0 for at least about 120 minutes;

wherein the composition further comprises an enteric coating that is resistant to dissolution in simulated gastric fluid or simulated intestinal fluid having a pH of 5.5 or less, wherein the composition provides for less than about 25% release of the peptide after two hours in said simulated gastric fluid or simulated intestinal fluid.

```
SEQUENCE LISTING

<160> NUMBER OF SEQ ID NOS: 3

<210> SEQ ID NO 1
<211> LENGTH: 8
<212> TYPE: PRT
<213> ORGANISM: Artificial Sequence
<220> FEATURE:
<223> OTHER INFORMATION: Synthetic polymer

<400> SEQUENCE: 1

Gly Gly Val Leu Val Gln Pro Gly
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic polymer

<400> SEQUENCE: 2

Gly Val Leu Val Gln Pro Gly
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic polymer

<400> SEQUENCE: 3

Val Leu Val Gln Pro Gly
1               5
```

2. The composition of claim 1, wherein the composition releases the peptide or salt thereof in the jejunum and ileum of a human patient.

3. The composition of claim 2, wherein the composition does not release the peptide or salt thereof in the duodenum.

4. The composition of claim 2, wherein the composition does not release the peptide or salt thereof in the colon.

5. The composition of claim 1, wherein the composition comprises a population of beads containing the matrix and an enteric coating.

6. The composition of claim 5, wherein the enteric coating comprises a co-polymer of methyl acrylate, methyl methacrylate, and methacrylic acid, and the ratio of free carbonyl groups to ester groups in the co-polymer is about 1:10.

7. The composition of claim 6, wherein the enteric coating is from about 15% to about 40% by weight of the composition.

8. The composition of claim 1, wherein the matrix comprises a synthetic polymer comprising one or more binders, fillers, or plasticizers.

9. The composition of claim 8, wherein the binder, filler, or plasticizer comprises one or more of a cellulose or cellulose derivative, fatty acid salt, and synthetic polymer.

10. The composition of claim 1, wherein the enteric coating comprises a plasticizer which is triethyl citrate.

11. The composition of claim 5, wherein the beads comprise a top coat or seal coat.

12. The composition of claim 1, wherein the composition is a capsule for oral delivery comprising a population of beads, the population of beads comprising from 0.25 to 2 mg of larazotide or larazotide derivative or salt thereof contained within an erodible polymer matrix comprising microcrystalline cellulose, the beads further comprising an enteric coating comprising a co-polymer of methyl acrylate, methyl methacrylate, and methacrylic acid.

13. The composition of claim 12, wherein the ratio of free carbonyl groups to ester groups in the co-polymer is about 1:10.

14. The composition of claim 12, wherein the enteric coating is from about 20% to about 30% of the total weight of the composition.

15. The composition of claim 9, wherein the one or more binders, fillers, or plasticizers comprises: a co-polymer of vinyl pyrrolidone and vinyl acetate, or one or more of ethyl cellulose, hydroxypropylmethyl cellulose (HPMC), and carboxymethyl cellulose; and a C8 to C18 fatty acid salt.

16. The composition of claim 15, wherein the C8 to C18 fatty acid salt is a salt of stearic acid.

17. The composition of claim 15, wherein the composition provides for sustained release of the peptide in simulated intestinal fluid having a pH of about 7.0 for at least about 180 minutes.

* * * * *